(12) United States Patent
Okakura et al.

(10) Patent No.: US 8,975,053 B2
(45) Date of Patent: Mar. 10, 2015

(54) THERMOSTABLE CATALASE

(75) Inventors: Kaoru Okakura, Odawara (JP); Fusuke Mazuka, Odawara (JP); Takayoshi Fukushima, Odawara (JP); Koichiro Murashima, Odawara (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 434 days.

(21) Appl. No.: 12/918,017

(22) PCT Filed: Feb. 18, 2009

(86) PCT No.: PCT/JP2009/052729
§ 371 (c)(1),
(2), (4) Date: Aug. 17, 2010

(87) PCT Pub. No.: WO2009/104622
PCT Pub. Date: Aug. 27, 2009

(65) Prior Publication Data
US 2010/0330646 A1 Dec. 30, 2010

(30) Foreign Application Priority Data
Feb. 18, 2008 (JP) .................... 2008-036171

(51) Int. Cl.
*C12N 9/08* (2006.01)
*C07H 21/04* (2006.01)

(52) U.S. Cl.
CPC ....... *C12Y 111/01006* (2013.01); *C12N 9/0065* (2013.01)
USPC .......................................... 435/192; 536/23.2

(58) Field of Classification Search
None
See application file for complete search history.

(56) References Cited

U.S. PATENT DOCUMENTS

| | | | |
|---|---|---|---|
| 5,071,439 A | 12/1991 | Weible | |
| 5,571,719 A | 11/1996 | Christensen et al. | |
| 5,646,025 A | 7/1997 | Moyer | |
| 6,159,720 A | 12/2000 | Murashima et al. | |
| 6,277,596 B1 | 8/2001 | Watanabe et al. | |
| 6,337,201 B1 | 1/2002 | Yanai et al. | |
| 6,403,362 B1 | 6/2002 | Moriya et al. | |
| 6,921,655 B1 | 7/2005 | Nakamura et al. | |
| 7,138,263 B2 | 11/2006 | Murashima et al. | |

FOREIGN PATENT DOCUMENTS

| | | |
|---|---|---|
| JP | 49-004956 A | 2/1974 |
| JP | 55-135588 A | 10/1980 |
| JP | 60-083579 A | 5/1985 |
| JP | 63-003788 A | 1/1988 |
| JP | 02-076579 A | 3/1990 |
| JP | 05-153975 A | 6/1993 |
| JP | 06-506347 A | 7/1994 |
| JP | 10179167 | 7/1998 |
| JP | 10-257883 A | 9/1998 |
| JP | 2001-017180 A | 1/2001 |
| JP | 2004-261137 A | 9/2004 |
| JP | 2007-143405 A | 6/2007 |
| WO | 92/17571 A1 | 10/1992 |
| WO | 96/34962 A1 | 11/1996 |
| WO | 97/34004 A1 | 9/1997 |
| WO | 98/03640 A1 | 1/1998 |
| WO | 98/03667 A1 | 1/1998 |
| WO | 98/11239 A1 | 3/1998 |
| WO | 00/24879 A1 | 5/2000 |
| WO | 00/68401 A1 | 11/2000 |
| WO | 01/90375 A1 | 11/2001 |
| WO | 03070956 | 8/2003 |
| WO | 2008049837 | 5/2008 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Extended European Search Report issued May 7, 2012, in corresponding EP Application No. 09711878.0 (in the name of Meiji Seika Kaisha, Ltd.).
EBI Accession No. EM_FUN: U97574, Oct. 1997, retreived from http://ibis.internal.epo.org/exam/dbfetch.jsp?id=EM_FUN:U97574.
Uniprot Accession No. 92405, Feb. 1997, retrieved from http://ibis.internal.epo.org/exam/dbfetch.jsp?id=UNIPROT:Q92405 on Apr. 19, 2012.
A.V. Kurakov et al., "Search for Micromycetes Producing Extracellular Catalase and Study of Conditions of Catalase Synthesis", Applied Biochemistry and Microbiology, 2001, 37(1): 59-64.
Ramesh Maheshwari et al., "Thermophilic Fungi: Their Physiology and Enzymes", Microbiology and Molecular Biology Reviews, 2000, 64(3): 461-488.
Gerben Straatsma et al., "Taxonomy of *Seytalidium thermophilum*, an important thermophilic fungus in mushroom compost", Mycol. Res., 1993, 97(3): 321-328.

(Continued)

*Primary Examiner* — Iqbal H Chowdhury
(74) *Attorney, Agent, or Firm* — Sughrue Mion, PLLC

(57) ABSTRACT

An object is to efficiently produce thermostable catalase at low cost by expressing it as a recombinant protein in large quantity.

A recombinant microorganism capable of efficiently expressing thermostable catalase can be provided by obtaining a DNA necessary for efficiently producing it as a recombinant protein, and the thermostable catalase can be efficiently produced at low cost by cultivating the obtained recombinant microorganism. Hydrogen peroxide can be efficiently decomposed at low cost, even at high temperature, by treating a solution containing hydrogen peroxide with the thermostable catalase of the present invention.

3 Claims, 2 Drawing Sheets

(56) References Cited

OTHER PUBLICATIONS

Norihiro Tsukagoshi, Kumikae Tanpakushitsu Seisan-hou Production of recombinant proteins, Japan Scientific Societies Press, pp. 94-95.

A. V. Kurakov et al., "Search for micromycetes producing extracellular catalase by micromycetes and study of conditions of catalase synthesis"., Prinkl. Biokhim. Mikrobiol. (ISSN 0555-1099), 2001, pp. 67-72, vol. 37, No. 1.

* cited by examiner

THERMOSTABLE CATALASE

TECHNICAL FIELD

The present invention relates to thermostable catalases, more particularly, thermostable catalases derived from *Penicillium pinophilum* or *Humicola grisea*, proteins having a thermostable catalase activity, DNAs encoding the proteins, and a process for producing the thermostable catalases.

BACKGROUND ART

Catalase is an enzyme which catalyzes a reaction in which hydrogen peroxide decomposes into water and oxygen. Hydrogen peroxide aqueous solution is widely used as an antiseptic or a disinfectant. After the completion of disinfection, the hydrogen peroxide solution can be easily removed with water, and is spontaneously decomposed as time progresses, and therefore, is widely used as a disinfectant for food. However, it is desired that hydrogen peroxide is completely decomposed and removed after use, because reactive oxygen species generated from any remaining hydrogen peroxide have a possibility of causing cell aging or cancer. Catalase is extremely useful for the decomposition of hydrogen peroxide, because no additional chemical substance is needed for the decomposition. Actually, catalase is used in decomposing and removing hydrogen peroxidase remained after bleaching of cotton or in food. Catalases derived from microorganisms (patent references 1 to 5) and catalases derived from animals, such as porcine or bovine liver catalase, are known.

Among such known catalases, catalase produced by a filamentous fungus *Aspergillus niger* or porcine liver catalase is widely used for industrial use. However, it is known that these catalases exhibit low thermostability and the remaining activity thereof after the treatment at 70° C. for 30 minutes was approximately 10% (patent reference 6). In particular, for the use of textile processing, food processing, or the like, catalase having thermostability higher than those of conventional catalases is desired, because hydrogen peroxide has to be decomposed at a high temperature. As thermostable catalases, catalases produced by *Aspergillus terreus* (patent reference 6), *Acremonium alabamensis* (patent reference 6), *Thermoascus aurantiacus* (patent reference 6), *Scytalidium thermophilum* (patent reference 7), *Humicola insolens* (patent reference 7), and genus *Thermomyces* (patent reference 8) have been reported.

It is known that filamentous fungi have an extremely high activity of secreting proteins, and are suitable as a host to produce a recombinant protein such as enzymes. Therefore, if a thermostable catalase gene can be introduced into a filamentous fungus and the thermostable catalase can be highly expressed as a recombinant protein, it is expected that the thermostable catalase can be produced at extremely high productivity in comparison with a wild type. With respect to the production of recombinant proteins, it has been reported that recombinant proteins could be produced in filamentous fungi classified into genus *Aspergillus* (patent reference 9), *Penicillium* (patent reference 10), *Humicola* (patent reference 11), *Trichoderma* (patent reference 12), or *Acremonium* (patent reference 13).

When a recombinant protein is expressed in these filamentous fungi as a host, all exogenous genes introduced into the host are not necessarily expressed. In general, it is considered preferable that the origin of an exogenous gene to be introduced is related to that of a host as closely as possible, in view of codon usage. For example, in the case that *Humicola insolens* was used as a host to express endoglucanase as a recombinant protein, a significant amount of endoglucanase was expressed when an NCE4 or NCE5 gene derived from *Humicola insolens* was introduced into *Humicola insolens* (patent references 14 and 15). By contrast, little amount of endoglucanase was expressed when an RCE I gene, which was derived from *Rhizopus oryzae* and had an amino acid sequence showing a high identity with those of NCE4 and NCE5, was introduced into *Humicola insolens* (patent reference 16). Further, in the case that *Aspergillus awamori* was used as a host to express glucoamylase as a recombinant protein, the introduction of a glucoamylase gene derived from *Aspergillus niger* resulted in high productivity (4.6 g/L), but the introduction of a glucoamylase gene derived from *Humicola grisea* resulted in low productivity (0.66 g/L) (non-patent reference 1). Furthermore, in the case that a-amylase was expressed as a recombinant protein, the introduction of an α-amylase gene derived from *Aspergillus oryzae* into *Aspergillus oryzae* as a host resulted in high productivity (12 g/L), but the introduction of the α-amylase gene derived from *Aspergillus oryzae* into *Trichoderma viride* resulted in only a productivity of 1 g/L (non-patent reference 1). These results show that, when a significant amount of recombinant protein is to be expressed, it is preferable to introduce a gene derived from a filamentous fungus which is the species same as or related to that of a host.

When a filamentous fungus is used as a host to express a large amount of thermostable catalase as a recombinant protein, it is considered preferable that the origin of a thermostable catalase gene to be introduced is closely related to the filamentous fungus as the host, as described above. However, with respect to the isolation of thermostable catalase genes, only a catalase gene derived from *Thermoascus aurantiacus* (patent reference 17) and a catalase gene derived from *Scytalidium thermophilum* (patent reference 18) have been reported. Thermostable catalase genes have not been isolated from filamentous fungi developed as a host for protein production, such as genus *Aspergillus, Penicillium, Humicola, Trichoderma*, or *Acremonium*, and therefore, it was very difficult to express thermostable catalase as a recombinant protein with high productivity.

[patent reference 1] Japanese Unexamined Patent Publication (kokai) No. 55-135588
[patent reference 2] Japanese Unexamined Patent Publication (kokai) No. 60-083579
[patent reference 3] Japanese Unexamined Patent Publication (kokai) No. 63-003788
[patent reference 4] Japanese Examined Patent Publication (kokoku) No. 49-004956
[patent reference 5] Japanese Unexamined Patent Publication (kokai) No. 2-076579
[patent reference 6] Japanese Unexamined Patent Publication (kokai) No. 5-153975
[patent reference 7] Japanese Translation Publication (Kohyo) No. 6-506347
[patent reference 8] Japanese Unexamined Patent Publication (kokai) No. 10-257883
[patent reference 9] International Publication WO 97/034004
[patent reference 10] International Publication WO 2000/068401
[patent reference 11] International Publication WO 98/003667
[patent reference 12] International Publication WO 98/011239
[patent reference 13] Japanese Unexamined Patent Publication (kokai) No. 2001/017180

[patent reference 14] International Publication WO 98/003640
[patent reference 15] International Publication WO 2001/090375
[patent reference 16] International Publication WO 2000/024879
[patent reference 17] Japanese Unexamined Patent Publication (kokai) No. 2004-261137
[patent reference 18] U.S. Pat. No. 5,646,025
[non-patent reference 1] Norihiro TSUKAGOSHI, Kumikae Tanpakushitsu Seisan-hou (Production of recombinant proteins), Japan Scientific Societies Press, pp. 94-95

DISCLOSURE OF THE INVENTION

Problems to be Solved by the Invention

Under the circumstances, the expression of a large amount of thermostable catalase as a recombinant protein is desired. An object to be solved by the present inventors is to search filamentous fungi belonging to genus *Aspergillus, Penicillium, Humicola, Trichoderma*, and *Acremonium*, which were developed as hosts for producing recombinant proteins, for thermostable catalases; to isolate genes encoding the thermostable catalases; and to express thermostable catalases in large quantity.

Means for Solving the Problems

To solve the object, the present inventors cultivated a number of filamentous fungi belonging to genus *Aspergillus, Penicillium, Humicola, Trichoderma*, and *Acremonium*, which had been developed as hosts for producing recombinant proteins; evaluated the thermostability of catalase contained in each culture liquid obtained; and attempted to find thermostable catalase from the filamentous fungi. As a result, the present inventors found that *Penicillium pinophilum* and *Humicola grisea* produced thermostable catalases.

Next, the present inventors purified thermostable catalase from the culture liquid of *Penicillium pinophilum*, and obtained a thermostable catalase in which a single band was observed at the position of approximately 80 kDa by SDS-polyacrylamide gel electrophoresis (SDS-PAGE) and the N-terminal amino acid sequence was DDSNAS-SETEAFLSEFYLNDNDAYLTTDVGG (SEQ ID NO.: 5). Further, the present inventors purified thermostable catalase from the culture liquid of *Humicola grisea*, and obtained a thermostable catalase in which a single band was observed at the position of approximately 80 kDa by SDS-polyacrylamide gel electrophoresis (SDS-PAGE) and the N-terminal amino acid sequence was QDTTSGQSPLAAYEVDDSTG (SEQ ID NO.: 10).

Furthermore, the present inventors succeeded in cloning genes encoding the above thermostable catalases from genomic DNAs of *Penicillium pinophilum* and *Humicola grisea*, and determining the nucleotide sequences of the genes, and the present invention was completed.

The present invention relates to:
1) a thermostable catalase produced by a microorganism belonging to genus *Penicillium;*
2) the thermostable catalase of 1), wherein the microorganism belonging to genus *Penicillium* is *Penicillium pinophilum;*
3) the thermostable catalase of 1) or 2), having a molecular weight of approximately 80 kDa;
4) a thermostable catalase produced by *Humicola grisea;*
5) the thermostable catalase of 4), having a molecular weight of approximately 80 kDa;
6) a protein selected from the group consisting of:
  (i) a protein comprising the amino acid sequence consisting of amino acids 1-692 of SEQ ID NO.: 2,
  (ii) a protein comprising an amino acid sequence in which one or plural amino acids are deleted, substituted, or added in the amino acid sequence consisting of amino acids 1-692 of SEQ ID NO.: 2, and having a thermostable catalase activity, and
  (iii) a protein comprising an amino acid sequence having a 70% or more identity with that consisting of amino acids 1-692 of SEQ ID NO.: 2, and having a thermostable catalase activity;
7) a protein consisting of the amino acid sequence consisting of amino acids 1-692 of SEQ ID NO.: 2, and having a thermostable catalase activity;
8) the protein of 6) or 7), having the amino acid sequence consisting of amino acids −1 to −42 of SEQ ID NO.: 2, or an amino acid sequence in which one or plural amino acids are deleted, substituted, or added in the amino acid sequence consisting of amino acids −1 to −42 of SEQ ID NO.: 2, at the N-terminal side of the protein;
9) a protein selected from the group consisting of:
  (i) a protein comprising the amino acid sequence consisting of amino acids 1-684 of SEQ ID NO.: 4,
  (ii) a protein comprising an amino acid sequence in which one or plural amino acids are deleted, substituted, or added in the amino acid sequence consisting of amino acids 1-684 of SEQ ID NO.: 4, and having a thermostable catalase activity, and
  (iii) a protein comprising an amino acid sequence having a 70% or more identity with that consisting of amino acids 1-684 of SEQ ID NO.: 4, and having a thermostable catalase activity;
10) a protein consisting of the amino acid sequence consisting of amino acids 1-684 of SEQ ID NO.: 4, and having a thermostable catalase activity;
11) the protein of 9) or 10), having the amino acid sequence consisting of amino acids −1 to −32 of SEQ ID NO.: 4, or an amino acid sequence in which one or plural amino acids are deleted, substituted, or added in the amino acid sequence consisting of amino acids −1 to −32 of SEQ ID NO.: 4, at the N-terminal side of the protein;
12) a DNA selected from the group consisting of:
  (i) a DNA encoding the protein of 6) to 8),
  (ii) a DNA comprising the nucleotide sequence consisting of nucleotides 1-2403 of SEQ ID NO: 1, and
  (iii) a DNA hybridizing under stringent conditions to a DNA consisting of the nucleotide sequence consisting of nucleotides 1-2403 of SEQ ID NO: 1, and encoding a protein having a thermostable catalase activity;
13) a DNA consisting of the nucleotide sequence consisting of nucleotides 1-2403 of SEQ ID NO: 1;
14) a DNA wherein an intron sequence is excised from the DNA of 12) or 13);
15) the DNA of 14), wherein the intron sequence is one or more sequences selected from the nucleotide sequence consisting of nucleotides 322-372, 599-651, 1068-1113, or 1279-1326 of SEQ ID NO: 1;
16) a DNA wherein a nucleotide sequence encoding a signal sequence is excised from the DNA of 12) to 15).
17) the DNA of 16), wherein the nucleotide sequence encoding a signal sequence is that consisting of nucleotides 1-126 of SEQ ID NO: 1;
18) a DNA selected from the group consisting of:
  (i) a DNA encoding the protein of 9) to 11),
  (ii) a DNA comprising the nucleotide sequence consisting of nucleotides 1-2749 of SEQ ID NO: 3, and (iii) a DNA hybridizing under stringent conditions to a DNA consisting of the nucleotide sequence consisting of nucleotides 1-2749 of SEQ ID NO: 3, and encoding a protein having a thermostable catalase activity;
19) a DNA consisting of the nucleotide sequence consisting of nucleotides 1-2749 of SEQ ID NO: 3;
20) a DNA wherein an intron sequence is excised from the DNA of 18) or 19):
21) the DNA of 20, wherein the intron sequence is one or more sequences selected from the nucleotide sequence consisting of nucleotides 283-463, 667-747, 771-846, 1008-1160, 1218-1270, or 1842-1895 of SEQ ID NO: 3;
22) a DNA wherein a nucleotide sequence encoding a signal sequence is excised from the DNA of 18) to 21);
23) the DNA of 22), wherein the nucleotide sequence encoding a signal sequence is that consisting of nucleotides 1-96 of SEQ ID NO: 3;
24) an expression vector comprising the DNA of 12) to 17);
25) a host microorganism transformed with the DNA of 12) to 17) or the expression vector of 24);
26) the host microorganism of 25), wherein the host microorganism is a filamentous fungus;
27) the host microorganism of 26), the filamentous fungus is a filamentous fungus belonging to genus *Aspergillus, Penicillium, Humicola, Trichoderma,* or *Acremonium;*
28) a process for producing a thermostable catalase, characterized by cultivating the host microorganism of 25) to 27), and collecting the thermostable catalase from the culture obtained by the cultivation;
29) an expression vector comprising the DNA of 18) to 23);
30) a host microorganism transformed with the DNA of 18) to 23) or the expression vector of 29);
31) the host microorganism of 30), wherein the host microorganism is a filamentous fungus;
32) the host microorganism of 31), the filamentous fungus is a filamentous fungus belonging to genus *Aspergillus, Penicillium, Humicola, Trichoderma,* or *Acremonium;* and
33) a process for producing a thermostable catalase, characterized by cultivating the host microorganism of 30) to 32), and collecting the thermostable catalase from the culture obtained by the cultivation.

Effects of the Invention

According to the present invention, DNAs necessary for efficiently producing thermostable catalase as a recombinant protein can be obtained, and recombinant microorganisms efficiently expressing thermostable catalase can be obtained. Further, thermostable catalase can be efficiently produced at low cost by cultivating the obtained microorganism. Hydrogen peroxide can be efficiently decomposed at low cost, even at high temperature, by treating a solution containing hydrogen peroxide with the thermostable catalase of the present invention.

BEST MODE FOR CARRYING OUT THE INVENTION

Figure 1:
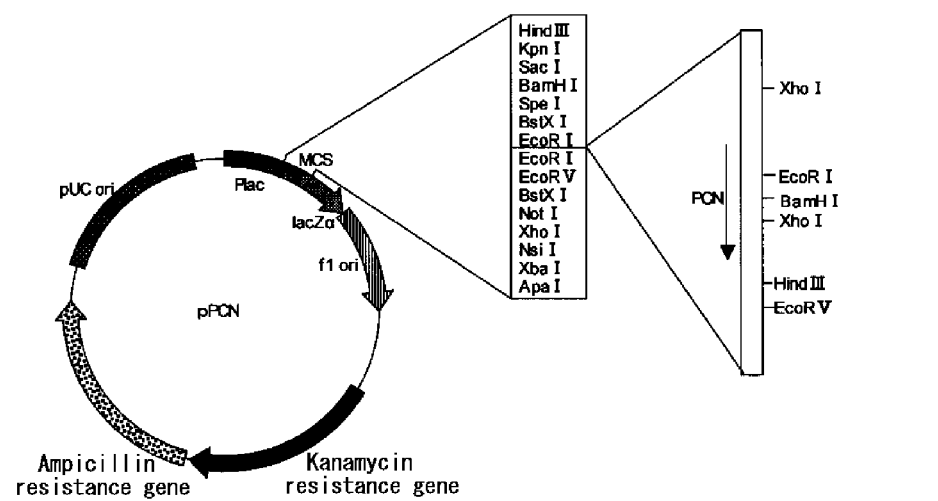
FIG. 1 is a restriction map of plasmid pPCN.
Figure 2:
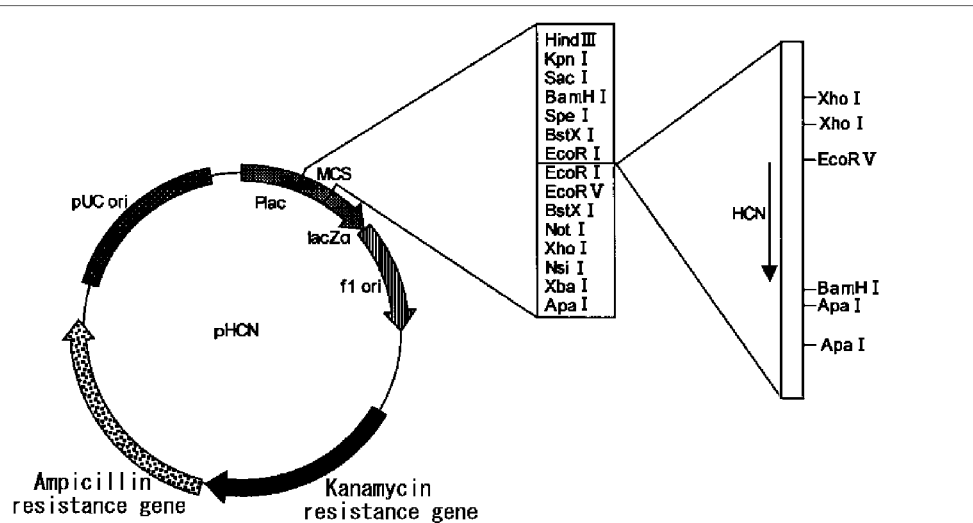
FIG. 2 is a restriction map of plasmid pHCN.

The term "thermostable catalase" as used herein means a catalase in which the percentage of the activity remaining after incubating at 70° C. for 30 minutes is 50% or more, as determined by measuring thermostability in accordance with the method described in Example 4 of patent reference 6.

Thermostable catalase produced by *Penicillium pinophilum* or *Humicola grisea* into a culture liquid may be obtained by, for example, a method disclosed in patent reference 6. A catalase activity may be evaluated by adding catalase to a solution containing hydrogen peroxide and quantifying the decrease in hydrogen peroxide during a predetermined period of time, for example, in accordance with a method disclosed in patent reference 6. Whether or not a catalase is thermostable may be judged, in accordance with a method disclosed in patent reference 6, by heat-treating a culture supernatant, which has been previously diluted to an appropriate concentration, at 70° C. for 30 minutes and measuring the catalase activities before and after the heat-treatment. According to the above definition as used herein, a catalase having a remaining activity of 50% or more after the heat-treatment is regarded as "thermostable catalase".

Culture supernatants of *Penicillium pinophilum* and *Humicola grisea* were obtained by the above method, and the thermostability of catalase contained in each supernatant was determined. As a result, the remaining activities after the heat-treatment at 70° C. for 30 minutes were 50% and 57% with respect to catalases produced by *Penicillium pinophilum* and *Humicola grisea*, respectively, and *Penicillium pinophilum* and *Humicola grisea* produced thermostable catalases.

The thermostable catalases may be purified from the themostable-catalase-containing culture supernatants obtained by the above method in accordance with one or more conventional methods for purifying proteins. As the methods, various commonly known methods may be applied: for example, a combination of hydrophobic chromatography and anion-exchange chromatography may be used. The molecular weight of each purified thermostable catalase may be determined by SDS-PAGE.

In accordance with the above methods, the thermostable catalases produced by *Penicillium pinophilum* and *Humicola grisea* were purified, and the molecular weight of each thermostable catalase was determined. Thermostable catalases having a molecular weight of approximately 80 kDa were obtained from *Penicillium pinophilum* and *Humicola grisea*.

The term "an amino acid sequence in which one or plural amino acids are deleted, substituted, or added in an amino acid sequence" as used herein means that the original amino acid sequence is modified by substitution or the like of plural amino acids which may naturally occur, or in accordance with a well-known method such as site-directed mutagenesis. The number of modified amino acids is preferably 1 to 50, more preferably 1 to 30, still more preferably 1 to 10, still more preferably 1 to 5, most preferably 1 to 2.

Preferred examples of a modified amino acid sequence in the protein according to the present invention may include an amino acid sequence in which one or plural amino acids (preferably one or several amino acids, or one, two, three, or four amino acids) are conservatively substituted.

The term "conservative substitution" as used herein means one or plural amino acid residues are replaced with different amino acids having similar chemical properties. Examples of the conservative substitution include a substitution of a hydrophobic residue for another hydrophobic residue, and a substitution of a polar residue for another polar residue having the same charge. Amino acids which have similar chemical properties and can be conservatively substituted with each other are known to those skilled in the art. More particularly, examples of nonpolar (hydrophobic) amino acids include alanine, valine, isoleucine, leucine, proline, tryptophan, phenylalanine, and methionine. Examples of polar (neutral)

amino acids include glycine, serine, threonine, tyrosine, glutamine, asparagine, and cysteine. Examples of basic amino acids having a positive charge include arginine, histidine, and lysine. Examples of acidic amino acids having a negative charge include aspartic acid and glutamic acid.

The term "under stringent conditions" as used herein means that a membrane after hybridization is washed at a high temperature in a solution of low salt concentration, for example, at 60° C. for 15 minutes in a solution of 0.5×SSC concentration (1×SSC: 15 mmol/L trisodium citrate and 150 mmol/L sodium chloride), preferably at 60° C. for 15 minutes in a solution of 0.5×SSC concentration with 0.1% SDS.

Hybridization is carried out in accordance with a known method. When a commercially available library is used, hybridization carried out in accordance with a method described in a protocol attached to the library.

The term "identity" with respect to nucleotide sequences or amino acid sequences as used herein means the degree of similarity between nucleotides or amino acid residues constituting sequences to be compared. The "identity" as used herein may be represented by a value calculated using a known homology search program. For example, the values may be easily calculated by using default parameters in FASTA or the like.

The amino acid sequence having a 70% or more identity with that consisting of amino acids 1-692 of SEQ ID NO.: 2 may be an amino acid sequence having an identity of, preferably 80% or more, more preferably 85% or more, still more preferably 90% or more, still more preferably 95% or more, still more preferably 98% or more, most preferably 99% or more.

The amino acid sequence having a 70% or more identity with that consisting of amino acids 1-684 of SEQ ID NO.: 4 may be an amino acid sequence having an identity of, preferably 80% or more, more preferably 85% or more, still more preferably 90% or more, still more preferably 95% or more, still more preferably 98% or more, most preferably 99% or more.

In the present invention, given the amino acid sequence consisting of amino acids 1-692 of SEQ ID NO.: 2, various nucleotide sequences encoding the amino acid sequence may be easily determined and selected.

In the present invention, given the amino acid sequence consisting of amino acids 1-684 of SEQ ID NO.: 4, various nucleotide sequences encoding the amino acid sequence may be easily determined and selected.

In the present invention, the DNA encoding a protein comprising the amino acid sequence consisting of amino acids 1-692 of SEQ ID NO.: 2 means not only part or all of the nucleotide sequence consisting of nucleotides 1-2403 of SEQ ID NO: 1, but also nucleotide sequences containing degenerate codons encoding the same amino acids. The present invention includes RNA sequences corresponding to these nucleotide sequences.

In the present invention, the DNA encoding a protein comprising the amino acid sequence consisting of amino acids 1-684 of SEQ ID NO.: 4 means not only part or all of the nucleotide sequence consisting of nucleotides 1-2749 of SEQ ID NO: 3, but also nucleotide sequences containing degenerate codons encoding the same amino acids. The present invention includes RNA sequences corresponding to these nucleotide sequences.

Preferred examples of the DNA encoding a protein comprising the amino acid sequence consisting of amino acids 1-692 of SEQ ID NO.: 2 include a DNA comprising the nucleotide sequence consisting of nucleotides 1-2403 of SEQ ID NO: 1.

Preferred examples of the DNA encoding a protein comprising the amino acid sequence consisting of amino acids 1-684 of SEQ ID NO.: 4 include a DNA comprising the nucleotide sequence consisting of nucleotides 1-2749 of SEQ ID NO: 3.

Genes encoding the thermostable catalases produced by *Penicillium pinophilum* and *Humicola grisea* can be isolated by preparing genomic phage libraries from *Penicillium pinophilum* and *Humicola grisea* and obtaining positive phage clones containing the thermostable catalase genes. As probes to screen the genomic phage libraries for positive phage clones, fragments of the thermostable catalase genes may be used. Each of the fragments of the thermostable catalase genes to be used as probes may be amplified by a PCR using each genomic DNA as a template. A primer set for the PCR may be designed based on conserved sequences among known catalase genes derived from filamentous fungi. The nucleotide sequence of each thermostable catalase gene may be determined by subcloning the thermostable catalase gene from an obtained positive clone into an *Escherichia coli* vector and analyzing the nucleotide sequence of the obtained vector. Intron sequences in the determined nucleotide sequence may be deduced on the basis of comparing the amino acid sequence deduced from the nucleotide sequence with those of known catalases, and conserved sequences of introns. Further, a sequence from the translation initiation codon of the gene to the codon immediately upstream of the sequence encoding the N-terminal amino acid sequence of a purified thermostable catalase, may be deduced as a sequence encoding a signal sequence.

The full-length of thermostable catalase gene PCN, which was isolated from genomic DNA of *Penicillium pinophilum* by the method described above, consisted of the 2403-bp nucleotide sequence of SEQ ID NO.: 1, and it was deduced that the gene included four introns having nucleotide sequences consisting of nucleotides 322-372, 599-651, 1068-1113, and 1279-1326 of SEQ ID NO: 1. The amino acid sequence of the thermostable catalase, deduced from the gene sequence, was that of SEQ ID NO.: 2. The amino acid sequence consisting of amino acids 1-31 of SEQ ID NO.: 2 was completely identical with the N-terminal amino acid sequence of the thermostable catalase purified from *Penicillium pinophilum*, and thus, it was deduced that the amino acid sequence consisting of amino acids −1 to −42 of SEQ ID NO.: 2 was a signal sequence and that the nucleotide sequence consisting of nucleotides 1-126 of SEQ ID NO: 1 was a nucleotide sequence encoding the signal sequence.

Based on the nucleotide sequence of catalase gene PCN derived from *Penicillium pinophilum*, primers for amplifying the gene of interest may be designed, a PCR may be carried out using genomic DNA from *Penicillium pinophilum* as a template, an expression vector may be constructed by ligating the amplified DNA fragment into an appropriate vector, and the gene of interest may be isolated. The DNA of the present invention derived from *Penicillium pinophilum* is contained in plasmid pPCN, and thus, the DNA or the plasmid may be used as a DNA template for PCR. An appropriate restriction enzyme may be used to prepare a desired DNA fragment from the plasmid.

According to the present invention, *Escherichia coli* transformed with pPCN is provided. This transformed *Escherichia coli* strain was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Feb. 7, 2008 (domestic deposit number:

FERM P-21504), and was transferred to an international deposit on Dec. 11, 2008 (international deposit number: FERM BP-11074).

The full-length of thermostable catalase gene HCN, which was isolated from genomic DNA of *Humicola grisea* by the method described above, consisted of a 2749-bp nucleotide sequence of SEQ ID NO.: 3, and it was deduced that the gene included six introns having nucleotide sequences consisting of nucleotides 283-463, 667-747, 771-846, 1008-1160, 1218-1270, and 1842-1895 of SEQ ID NO: 3. The amino acid sequence of the thermostable catalase, deduced from the gene sequence, was that of SEQ ID NO.: 4. The amino acid sequence consisting of amino acids 1-20 of SEQ ID NO.: 4 was completely identical with the N-terminal amino acid sequence of the thermostable catalase purified from Humicola grisea, and thus, it was deduced that the amino acid sequence consisting of amino acids -1 to -32 of SEQ ID NO.: 4 was a signal sequence and that the nucleotide sequence consisting of nucleotides 1-96 of SEQ ID NO: 3 was a nucleotide sequence encoding the signal sequence.

Based on the nucleotide sequence of catalase gene HCN derived from *Humicola grisea*, primers for amplifying the gene of interest may be designed, a PCR may be carried out using genomic DNA from *Humicola grisea* as a template, an expression vector may be constructed by ligating the amplified DNA fragment into an appropriate vector, and the gene of interest may be isolated. The DNA of the present invention derived from *Humicola grisea* is contained in plasmid pHCN, and thus, the DNA or the plasmid may be used as a DNA template for PCR. An appropriate restriction enzyme may be used to prepare a desired DNA fragment from the plasmid.

According to the present invention, *Escherichia coli* transformed with pHCN is provided. This transformed *Escherichia coli* strain was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Feb. 7, 2008 (domestic deposit number: FERM P-21503), and was transferred to an international deposit on Dec. 11, 2008 (international deposit number: FERM BP-11073).

Each of the thermostable catalase genes, isolated as described above, may be introduced into a host, and a desired thermostable catalase may be produced by expressing it in the host. The DNA to be introduced into the host may be the full-length of a thermostable catalase gene, a DNA obtained by excising part of all of intron sequences from the full-length DNA, or a DNA obtained by excising the nucleotide sequence encoding a signal sequence.

According to the present invention, an expression vector comprising the DNA of the present invention, in which the DNA can be replicated in a host microorganism and a protein encoded by the DNA can be expressed, is provided. Further, according to the present invention, a microorganism transformed with this expression vector is provided.

The host-vector system is not particularly limited. For example, a system using *Escherichia coli*, actinomycetes, yeasts, or fungi, or a fusion protein expression system using the same may be used. Examples of a preferred host microorganism used in the present invention include filamentous fungi, more preferably genus *Trichoderma*, genus *Aspergillus*, genus *Penicillium* (most preferably *Penicillium pinophilum*), genus *Humicola* (most preferably *Humicola grisea*), and genus *Acremonium*. As an expression vector, expression vectors disclosed in patent references 9 to 13 may be used.

The expression vector of the present invention may be constructed in accordance with procedures and methods widely used in the field of genetic engineering.

The expression vector of the present invention may include not only the DNA of the present invention, but also a DNA capable of regulating the expression of the DNA, a genetic marker to select a transformant, or the like, to express a desired protein by incorporating the expression vector into a host microorganism.

The obtained transformant may be cultivated in an appropriate medium, and the protein of the present invention may be obtained by isolating it from the culture. The cultivation of the transformant and the conditions thereof may be appropriately selected in accordance with the microorganism used. The protein of interest may be collected and purified from the culture liquid in accordance with conventional methods.

EXAMPLES

The present invention now will be further illustrated by, but is by no means limited to, the following Examples.

Example 1

Measurement of Catalase Activity (Thermostability) in Culture Liquid of *Penicillium Pinophilum*

*Penicillium pinophilum* grown on potato dextrose agar was inoculated in a 200 mL conical flask containing 30 mL of a medium (50 g/L sucrose, 20 g/L malt extract, and 5 g/L yeast extract), and cultivated at 26° C. for 5 days with shaking. The cells were removed from the resulting culture liquid by centrifugation to obtain the culture supernatant. The catalase activity (thermostability) of catalase contained in the resulting culture supernatant was measured by the method described in Example 4 of patent reference 6. The percentage of the remaining activity after incubating at 70° C. for 30 minutes was 50%. It was concluded from the result that *Penicillium pinophilum* produced thermostable catalase.

Example 2

Isolation and Purification of Thermostable Catalase in Culture Liquid of *Penicillium Pinophilum*

Ammonium sulfate was dissolved in the culture supernatant of *Penicillium pinophilum*, obtained in the method described in Example 1, at a final concentration of 1 mol/L. The resulting solution was subjected and adsorbed to a hydrophobic column Phenyl Sepharose HP 26/10 (manufactured by GE Healthcare bioScience), which had been previously equilibrated with a 50 mmol/L phosphate buffer (pH7.0) containing 1 mol/L ammonium sulfate. Proteins adsorbed to the hydrophobic column were eluted and fractionated by a linear gradient elution method from a 50 mmol/L phosphate buffer (pH7.0) containing 1 mol/L ammonium sulfate to a 50 mmol/L phosphate buffer (pH7.0). A catalase activity of each fractionated eluate was measured by the method described in Example 1, and fractions having the activity were collected. Ammonium sulfate was added to the collected active fraction at a final concentration of 1 mol/L, and the above procedure was repeated to carry out rechromatography using the hydrophobic column. The resulting active fraction was concentrated and desalted by ultrafiltration, and adjusted to a final concentration of 50 mmol/L with a phosphate buffer (pH8.0). This solution was subjected to an anion-exchange column MonoQ (manufactured by GE healthcare Bioscience), which had been previously equilibrated with a 50 mmol/L phosphate buffer (pH8.0) containing 1 mol/L ammonium sulfate, and proteins were adsorbed to the column. The adsorbed proteins were eluted and fractionated by a linear gradient elution method from a 50 mmol/L phosphate buffer (pH8.0) to a 50 mmol/L phosphate buffer (pH8.0) containing 1 mol/L NaCl. A catalase activity (thermostability) of each fractionated eluate was measured by the method described in Example 1, and fractions having the activity were collected. The collected active fraction was analyzed by SDS-PAGE to detect a single band of approximately 80 kDa, and it was judged that the protein detected as the band is a thermostable catalase. The thermostable catalase was separated by SDS-PAGE and blotted on a polyvinylidene difluoride (PVDF) membrane. The N-terminal amino acid sequence was analyzed to obtain the following sequence:

```
DDSNASSETEAFLSEFYLNDNDAYLTTDVGG    (SEQ ID NO.: 5)
```

Example 3

Cloning of Thermostable Catalase Gene PCN from *Penicillium Pinophilum*

3-1) Preparation of Genomic DNA Library

Genomic DNA was isolated and purified from *Penicillium pinophilum* cells in accordance with the method of Horiuchi et al. [H. Horiuchi et al., J. Bacteriol., 170, 272-278, (1988)]. The isolated genomic DNA was partially digested with restriction enzyme Sau3AI. The resulting DNA fragments were ligated with BamHI arms of a phage vector EMBL3 cloning kit (manufactured by Stratagene) using a ligation kit Ver. 2 (manufacture by Takara Bio). The mixture was precipitated with ethanol and dissolved in a TE buffer. The whole amount of the ligated mixture and a MaxPlaxλ packerging kit (manufactured by Epicenter Technologies) were used to form phage particles, and an *Escherichia coli* XL1-blue MRA (P2) strain was infected with the phage particles. As a result, a genomic DNA library composed of $1.1 \times 10^4$ phages was obtained.

3-2) Preparation of Probe

The following primers ware prepared based on conserved sequences among known catalases:

```
P catalase F:
GAGGCCGGCAACTACCCNGARTGGRA    (SEQ ID NO.: 6)

P catalase R:
CCTGCTCGGTCTCGGCRAARWARTT     (SEQ ID NO.: 7)
```

The P catalase F and P catalase R primers and genomic DNA were used as primers and a template, respectively, to carry out a PCR. LA Taq polymerase (manufactured by Takara Bio) was used in the PCR. In the PCR, a cycle composed of a reaction at 94° C. for 30 seconds, annealing for 30 seconds, and a reaction at 72° C. for 1 minute was repeated 40 times. In this regard, the annealing temperature in the first 20 cycles was stepwisely lowered from 63° C. to 53° C., and the annealing temperature in the subsequent 20 cycles was 53° C. The amplified DNA fragment of 250 by was inserted into a pCR2.1-TOPO plasmid vector, using a TOPO TA cloning kit (manufactured by Invitrogen) in accordance with a protocol attached to the kit, to obtain plasmid TOPO-P catalase.

The cloned DNA fragment inserted into plasmid TOPO-P catalase was sequenced using a BigDye(R) Terminator v3.1 Cycle Sequencing Kit (manufactured by Applied Biosystems) and an ABI PRISM genetic analyzer (manufactured by Applied Biosystems) in accordance with protocols attached thereto. The determined nucleotide sequence was used to carry out a homology search. As a result, the nucleotide sequence showed a 71% identity with that of a catalase derived from *Aspergillus clavatus*, and thus, it was judged that the DNA fragment was part of a catalase gene. The DNA fragment was amplified by a PCR using plasmid TOPO-P catalase in a fashion substantially similar to that described above, and the obtained PCR product was labeled using an ECL direct system (manufactured by Amersham Pharmacia Biotech) as a probe.

3-3) Screening by Plaque Hybridization

Phage plaques prepared in Example 3-1 were transferred to a Hybond N+ Nyron Transfer Membrane (manufactured by Amersham). The membrane was denatured with alkali, washed with 5×SSC (SSC: 15 mmol/L trisodium citrate and 150 mmol/L sodium chloride), and dried to immobilize DNAs. After a prehybridization at 42° C. for 1 hour, the probe labeled with horseradish peroxidase (HRP) was added, and a hybridization at 42° C. for 4 hours was carried out. The probe was washed with 0.5×SSC containing 6 mol/L urea and 0.4% SDS twice, and washed with 2×SSC twice.

After the probe was washed, the nylon membrane was immersed in a detection solution for 1 minute, and exposed to a hyperfilm ECL (manufactured by Amersham) to obtain a positive clone. The preparation of DNA from the positive clone was carried out by using LE392 as a host *Escherichia coli* in accordance with the method of Maniatis et al. (J. Sambrook, E. F. Fritsch and T. Maniatis, "Molecular Cloning", Cold Spring Harbor Laboratory Press. 1989). LE392 was cultivated in an LB-MM medium (1% peptone, 0.5% yeast extract, 0.5% sodium chloride, 10 mmol/L magnesium sulfate, and 0.2% maltose) overnight. The culture was infected with a phage solution derived from a single plaque, and cultivated in the LB-MM medium overnight. Sodium chloride and chloroform were added to the culture at final concentrations of 1 mol/L and 0.8%, respectively, to promote the lysis of *Escherichia coli*. The *Escherichia coli* cell debris was removed by centrifugation, and phage particles were collected from a polyethylene glycol (PEG) precipitate (10% PEG6000). The phage particles were digested with proteinase K in the presence of SDS, treated with phenol, and precipitated with ethanol, to collect phage DNA.

The obtained DNA and the ECL direct system were used to carry out Southern blotting. A hybridization was carried out using the PCR-amplified fragment described in Example 3-2 as a probe. As a result, a PstI fragment of approximately 7 kb showed common hybridization patterns to those of chromosomal DNA.

The PstI fragment was cloned into pUC118 to obtain plasmid pUC-PCN. The nucleotide sequence of the obtained plasmid was determined by the method described in Example 3-2. To subclone catalase gene PCN derived from *Penicillium pinophilum*, a PCR using pUC-PCN as a template and the following primer set (PCNF and PCNR) was carried out to amplify the PCN gene.

```
PCNF:  ATGCGAGGATTATACTCCCTC    (SEQ ID NO.: 8)

PCNR:  CTACTCATCCACAGCGAATCG    (SEQ ID NO.: 9)
```

The amplified DNA was inserted into a pCR2.1-TOPO plasmid vector using a TOPO TA cloning kit (manufactured by Invitrogen) to obtain plasmid pPCN. An *Escherichia coli* TOP10 strain (Invitrogen) was transformed with plasmid pPCN to obtain *Escherichia coli* TOP10/pPCN.

3-4) Deduction of Amino Acid Sequence of Thermostable Catalase

The full-length of thermostable catalase gene PCN, which was isolated from genomic DNA of *Penicillium pinophilum* by the method described above, consisted of the 2403-bp nucleotide sequence of SEQ ID NO.: 1. On the basis of comparing the amino acid sequence deduced from the nucleotide sequence with those of known catalases, and conserved sequences of introns, it was deduced that the gene included four introns having nucleotide sequences consisting of nucleotides 322-372, 599-651, 1068-1113, and 1279-1326 of SEQ ID NO: 1. The amino acid sequence of the thermostable catalase, deduced from the nucleotide sequence, was that of SEQ ID NO.: 2. The amino acid sequence consisting of amino acids 1-31 of SEQ ID NO.: 2 was completely identical with the N-terminal amino acid sequence (shown in Example 2) of the thermostable catalase purified from *Penicillium pinophilum*, and thus, it was deduced that the amino acid sequence consisting of amino acids −1 to −42 of SEQ ID NO.: 2 was a signal sequence and that the nucleotide sequence consisting of nucleotides 1-126 (encoding the amino acids −1 to −42 of SEQ ID NO.: 2) of SEQ ID NO: 1 was a nucleotide sequence encoding the signal sequence.

Example 4

Measurement of Catalase Activity (Thermostability) in Culture Liquid of *Humicola Grisea*

A culture supernatant of *Humicola grisea* was prepared in a fashion substantially similar to that described in Example 1. The catalase activity (thermostability) of catalase contained in the resulting culture supernatant was measured by the method described in Example 1. The percentage of the remaining activity after incubating at 70° C. for 30 minutes was 57%. It was concluded from the result that *Humicola grisea* produced thermostable catalase.

Example 5

Isolation and Purification of Thermostable Catalase in Culture Liquid of *Humicola Grisea*

Ammonium sulfate was dissolved in the culture supernatant of *Humicola grisea*, obtained in the method described in Example 4, at a final concentration of 1 mol/L. The resulting solution was subjected and adsorbed to a hydrophobic column Phenyl Sepharose HP 26/10 (manufactured by GE Healthcare bioScience), which had been previously equilibrated with a 50 mmol/L phosphate buffer (pH7.0) containing 1 mol/L ammonium sulfate. Proteins adsorbed to the hydrophobic column were eluted and fractionated by a linear gradient elution method from a 50 mmol/L phosphate buffer (pH7.0) containing 1 mol/L ammonium sulfate to a 50 mmol/L phosphate buffer (pH7.0). A catalase activity of each fractionated eluate was measured by the method described in Example 1, and fractions having the activity were collected. Ammonium sulfate was added to the collected active fraction at a final concentration of 1 mol/L, and the above procedure was repeated to carry out rechromatography using the hydrophobic column. The resulting active fraction was concentrated and desalted by ultrafiltration, and adjusted to a final concentration of 50 mmol/L with an acetate buffer (pH4.0). This solution was subjected to a cation-exchange column MonoS (manufactured by GE healthcare Bioscience), which had been previously equilibrated with a 50 mmol/L acetate buffer (pH4.0). The catalase activity was detected in the non-adsorbed fraction, and thus, the non-adsorbed fraction was collected as the active fraction. The collected active fraction was analyzed by SDS-PAGE to detect a single band of approximately 80 kDa, and it was judged that the protein detected as the band is a thermostable catalase. The thermostable catalase was separated by SDS-PAGE and blotted on a PVDF membrane. The N-terminal amino acid sequence was analyzed to obtain the following sequence:

QDTTSGQSPLAAYEVDDSTG      (SEQ ID NO.: 10)

Example 6

Cloning of Thermostable Catalase Gene HCN from *Humicola Grisea*

6-1) Preparation of Genomic DNA Library

A genomic DNA library of Humicola grisea was prepared by the method described in Example 3-1.

6-2) Preparation of Probe

The following primers ware prepared based on conserved sequences among catalases derived from filamentous fungi and yeasts:

H catalase F:  GTNCGNTTYTCNACTGT   (SEQ ID NO.: 11)

H catalase R:  AARAANACGGNTTRTTGTT (SEQ ID NO.: 12)

[The underlined abbreviation "N" at the 12th position of SEQ ID NO.: 12 stands for deoxyinosine.]

The H catalase F and H catalase R primers and genomic DNA were used as primers and a template, respectively, to carry out a PCR. Ex Taq polymerase (manufactured by Takara Bio) was used in the PCR. In the PCR, a cycle composed of a reaction at 98° C. for 10 seconds, annealing at 55° C. for 30 seconds, and an elongation reaction at 72° C. for 15 seconds was repeated 30 times. The amplified DNA fragment of 300 by was inserted into a pCR2.1-TOPO plasmid vector, using a TOPO TA cloning kit (manufactured by Invitrogen) in accordance with a protocol attached to the kit, to obtain plasmid TOPO-H catalase.

The cloned DNA fragment inserted into plasmid TOPO-H catalase was sequenced, and the determined nucleotide sequence was used to carry out a homology search. As a result, the nucleotide sequence showed a 97% identity with that of a catalase derived from *Sclerotinia sclerotiorum*, and thus, it was judged that the DNA fragment was part of a catalase gene. The DNA fragment was amplified by a PCR using plasmid TOPO-H catalase in a fashion substantially similar to that described above, and the obtained PCR product was labeled using an ECL direct system (manufactured by Amersham Pharmacia Biotech) as a probe.

6-3) Screening by Plaque Hybridization

The genomic DNA library was screened in accordance with the method described in Example 3-3, and a positive clone was obtained. The obtained positive clone was analyzed by Southern blotting. As a result, an XhoI fragment of approximately 7 kb and a BamHI fragment of approximately 4 kb showed common hybridization patterns to those of chromosomal DNA. The XhoI fragment and the BamHI fragment were separately cloned into pUC118 to obtain plasmid pUC-HCN-XhoI and plasmid pUC-HCN-BamH1, respectively. The nucleotide sequences of these plasmids were determined. As a result, the XhoI fragment contained the sequence from the 616th nucleotide to the 3'-terminus of SEQ ID NO.: 3 and the BamHI fragment contained the sequence from the 5'-terminus to the 1675th nucleotide of SEQ ID NO.: 3, and thus, these fragments contained thermostable catalase gene fragments. These nucleotide sequences were joined to determine that of the full-length of a thermostable catalase gene. To subclone catalase gene HCN derived from *Humicola grisea*, a PCR using genomic DNA of *Humicola grisea* as a template and the following primer set (HCNF and HCNR) was carried out to amplify the HCN gene.

```
HCNF:  ATGAACAGAGTCACGAATCTC   (SEQ ID NO.: 13)
HCNR:  TCAAAAAACAAAGGCACCAAG   (SEQ ID NO.: 14)
```

The amplified DNA was inserted into a pCR2.1-TOPO plasmid vector using a TOPO TA cloning kit (manufactured by Invitrogen) to obtain plasmid pHCN. An *Escherichia coli* TOP10 strain (Invitrogen) was transformed with plasmid pHCN to obtain *Escherichia coli* TOP10/pHCN.

6-4) Deduction of Amino Acid Sequence of Thermostable Catalase

The full-length of thermostable catalase gene HCN, which was isolated from genomic DNA of *Humicola grisea* by the method described above, consisted of the 2749-bp nucleotide sequence of SEQ ID NO.: 3. On the basis of comparing the amino acid sequence deduced from the nucleotide sequence with those of known catalases, and conserved sequences of introns, it was deduced that the gene included six introns having nucleotide sequences consisting of nucleotides 283-463, 667-747, 771-846, 1008-1160, 1218-1270, and 1842-1895 of SEQ ID NO: 3. The amino acid sequence of the thermostable catalase, deduced from the nucleotide sequence, was that of SEQ ID NO.: 4. The amino acid sequence consisting of amino acids 1-20 of SEQ ID NO.: 4 was completely identical with the N-terminal amino acid sequence (shown in Example 5) of the thermostable catalase purified from *Humicola grisea*, and thus, it was deduced that the amino acid sequence consisting of amino acids −1 to −32 of SEQ ID NO.: 4 was a signal sequence and that the nucleotide sequence consisting of nucleotides 1-96 (encoding the amino acids −1 to −32 of SEQ ID NO.: 4) of SEQ ID NO: 3 was a nucleotide sequence encoding the signal sequence.

Example 7

Preparation of Expression Vector for Recombinant PCN

An expression of recombinant PCN using *Aspergillus niger* var. macrosporus as a host was carried out by using an expression vector in which the PCN gene was inserted between the promoter and the terminator of a proctase B gene, which was remarkably expressed in *Aspergillus niger* var. macrosporus. The expression vector was prepared in accordance with the following procedures.

7-1) Preparation of Genomic DNA Library

Genomic DNA was isolated and purified from *Aspergillus niger* var. macrosporus cells in accordance with the method of Horiuchi et al. [H. Horiuchi et al., J. Bacteriol., 170, 272-278, (1988)]. The isolated genomic DNA was partially digested with restriction enzyme Sau3AI. The resulting DNA fragments were ligated with BamHI arms of a phage vector λEMBL3 cloning kit (manufactured by Stratagene) using a ligation kit Ver. 2 (manufactured by Takara Bio). The mixture was precipitated with ethanol and dissolved in a TE buffer. The whole amount of the ligated mixture and a MaxPlaxλ packerging kit (manufactured by Epicenter Technologies) were used to form phage particles, and an *Escherichia coli* XL1-blue MRA (P2) strain was infected with the phage particles. As a result, a genomic DNA library composed of $1.25\times 10^5$ phages was obtained.

7-2) Preparation of Probe

With respect to the genomic DNA library of *Aspergillus niger* var. macrosporus, Southern blotting was carried out using the coding region of the proctase B gene as a probe to isolate a clone containing the promoter and terminator regions of the proctase B gene. The coding region of the proctase B was amplified by a PCR using genomic DNA of *Aspergillus niger* var. macrosporus as a template and the following primers (proctaseB-N and proctaseB-C), which were designed based on the 5'- and 3'-termini of the coding region of the proctase B disclosed in Japanese Unexamined Patent Publication (kokai) No. 5-68570.

```
proctaseB-N:  ATGGTCGTCTTCAGCAAAACC (SEQ ID NO.: 15)
proctaseB-C:  CTAAGCCTGAGCGGCGAATCC (SEQ ID NO.: 16)
```

The PCR was carried out using an LA PCR™ KIT Ver2.1 (manufactured by Takara Bio). In the PCR, after an incubation at 94° C. for 1 minute, a cycle composed of a reaction at 94° C. for 30 seconds, a reaction at 52° C. for 30 seconds, and a reaction at 72° C. for 90 seconds was repeated 30 times, and a reaction at 72° C. for 7 minutes was carried out to complete the PCR. As a result, a DNA of approximately 1.2 kb was amplified. The amplified DNA fragment of 1.2 kb was inserted into a pCR2.1-TOPO plasmid vector, using a TOPO TA cloning kit (manufactured by Invitrogen) in accordance with a protocol attached to the kit, to obtain plasmid TOPO-ProB. The cloned DNA fragment inserted into plasmid TOPO-ProB was sequenced using a BigDye(R) Terminator v3.1 Cycle Sequencing Kit (manufactured by Applied Biosystems) and an ABI PRISM genetic analyzer (manufactured by Applied Biosystems) in accordance with protocols attached thereto. The determined nucleotide sequence accorded with that of the proctase B gene disclosed in Japanese Unexamined Patent Publication (kokai) No. 5-68570, and thus, it was judged that the DNA fragment was the coding region of the proctase B gene. The DNA fragment was labeled using an ECL direct system (manufactured by Amersham Pharmacia Biotech) as a probe.

7-3) Screening of Clone Containing Promoter and Terminator Regions of Proctase Gene by Plaque Hybridization Phage plaques prepared in Example 7-1 were transferred to a Hybond N+ Nyron Transfer Membrane (manufactured by Amersham). The membrane was denatured with alkali, washed with 5×SSC (SSC: 15 mmol/L trisodium citrate and 150 mmol/L sodium chloride), and dried to immobilize DNAs. After a prehybridization at 42° C. for 1 hour, the probe prepared by the method described in Example 7-2 was added, and a hybridization at 42° C. for 20 hours was carried out. The probe was washed with 0.5×SSC containing 6 mol/L urea and 0.4% SDS twice, and washed with 2×SSC twice. After the probe was washed, the nylon membrane was immersed in a detection solution for 1 minute, and exposed to a hyperfilm ECL (manufactured by Amersham) to obtain eight positive clones.

The preparation of DNA from each of the positive clones was carried out by using LE392 as a host *Escherichia coli* in accordance with the method of Maniatis et al. (J. Sambrook, E. F. Fritsch and T. Maniatis, "Molecular Cloning", Cold Spring Harbor Laboratory Press. 1989). LE392 was cultivated in an LB-MM medium (1% peptone, 0.5% yeast extract, 0.5% sodium chloride, 10 mmol/L magnesium sulfate, and 0.2% maltose) overnight. The culture was infected with a phage solution derived from a single plaque, and cultivated in the LB-MM medium overnight. Sodium chloride and chloroform were added to the culture at final concentrations of 1 mol/L and 0.8%, respectively, to promote the lysis of *Escherichia coli*. The *Escherichia coli* cell debris was removed by centrifugation, and phage particles were collected from a polyethylene glycol (PEG) precipitate (10% PEG6000). The phage particles were digested with proteinase K in the presence of SDS, treated with phenol, and precipitated with ethanol, to collect phage DNA.

The obtained DNA and the ECL direct system were used to carry out Southern blotting. A hybridization was carried out using the probe prepared by the method described in Example 7-2. As a result, an XhoI-EcoRI fragment of approximately 5.5 kb showed common hybridization patterns to those of chromosomal DNA. It was judged that the DNA fragment contained the proctase B gene, and then, subcloning of the DNA fragment was carried out. The XhoI-EcoRI fragment excised from the phage DNA was inserted between the SalI and EcoRI sites of pUC119 to obtain plasmid pPROB/119E.X. The nucleotide sequence of the obtained plasmid was sequenced to determine those of the promoter and terminator regions of the proctase B gene.

7-4) Construction of Recombinant Vector pPTB-EX for Gene Expression

A vector in which the coding region of the proctase B gene was excised from plasmid pPROB/119E.X prepared by the method described in Example 7-3 and the 3'-terminus of the promoter region of the gene was ligated to the 5'-terminus of the terminator region of the gene via the XbaI recognition sequence, was designated expression vector pPTB-EX. The expression vector pPTB-EX was prepared by an inverse PCR using pPROB/119E.X as a template and the following primers (proctaseBNxba and proctaseBCxba) designed based on the 3'-terminus of the promoter and the 5'-terminus of the terminator of the proctase B gene, respectively.

```
proctaseBNxba:
GGTCTAGAATGTCAAGCAAGAGAGT        (SEQ ID NO.: 17)

proctaseBCxba:
GGTCTAGAATCAACCACTGAAGTGGA       (SEQ ID NO.: 18)
```

In this regard, the XbaI recognition sequence was added to the 5'-terminus of each primer. Primestar MAX DNA POLYMERASE (manufactured by Takara Bio) was used in the inverse PCR, in which a cycle composed of a reaction at 98° C. for 10 seconds, a reaction at 55° C. for 5 seconds, and a reaction at 72° C. for 60 seconds was repeated 30 times. As a result, a DNA fragment of approximately 7 kb was amplified. The resulting PCR reaction liquid and a QIAQUICK PCR PURIFICATION KIT (manufactured by Qiagen) were used to purify the DNA fragment. The DNA fragment was dissolved in 50 μL of a TE buffer, digested with restriction enzyme XbaI, and re-ligated using a ligation kit Ver. 2 (manufacture by Takara Bio) to obtain the expression vector pPTB-EX. The nucleotide sequence of the obtained plasmid was analyzed, and it was confirmed that the inverse PCR caused no mutations.

7-5) Construction of Vector pPTPCN for Recombinant PCN Expression

The PCN gene isolated by the method described in Example 3 was inserted into the XbaI site of expression vector pPTB-EX to construct vector pPTPCN for expressing recombinant PCN. To add the XbaI recognition sequence to the 5'- and 3'-termini of the coding region of the PCN gene, a PCR was carried out using pPCN as a template and the following primers (PCN-XbaIPtN and PCN-XbaIPtC) in which the XbaI recognition sequence was added to the 5'- and 3'-termini of the coding region of the PCN gene.

```
PCN-XbaIPtN:
GGTCTAGAGGTCAAAATGCGAGGATTATACTCCCT(SEQ ID NO.: 19)

PCN-XbaIPtC:
GGTCTAGACTACTCATCCACAGCGAATCGG       (SEQ ID NO.: 20)
```

Figure 3:
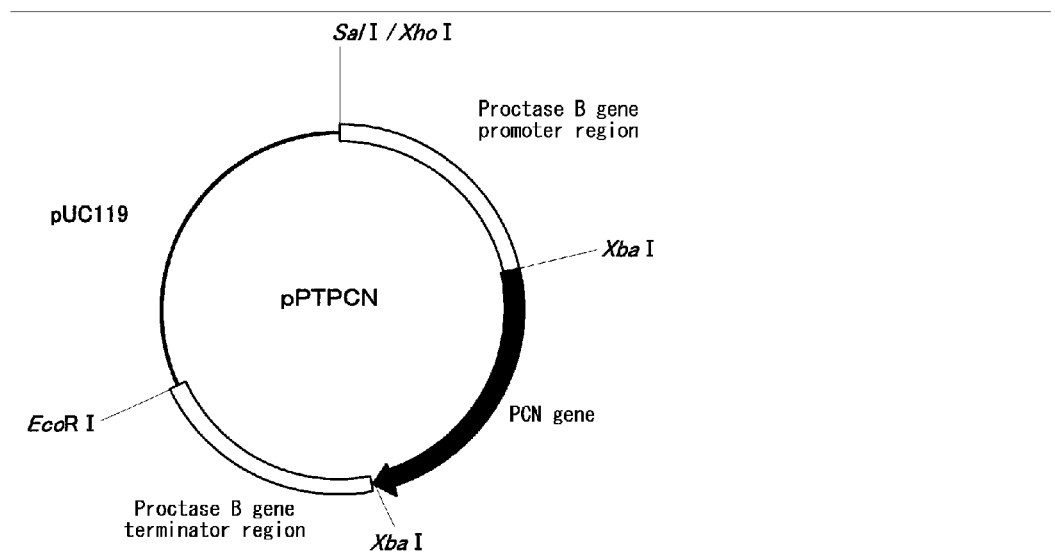
FIG. 3 is a restriction map of plasmid pPTPCN.

Primestar MAX DNA POLYMERASE (manufactured by Takara Bio) was used in the PCR, in which a cycle composed of a reaction at 98° C. for 10 seconds, a reaction at 55° C. for 5 seconds, and a reaction at 72° C. for 60 seconds was repeated 30 times. As a result, a DNA fragment of approximately 2.3 kb was amplified. The resulting PCR reaction liquid and a QIAQUICK PCR PURIFICATION KIT (manufactured by Qiagen) were used to purify the DNA fragment. The DNA fragment was dissolved in 50 μL of a TE buffer, and digested with restriction enzyme XbaI. The digested fragment was ligated using a ligation kit Ver. 2 (manufacture by Takara Bio) to pPTB-EX, which had been digested with XbaI and dephosphorylated, to obtain plasmid pPTPCN (SEQ ID NO.: 21, FIG. 3). The DNA sequence of the PCN gene inserted into the plasmid was analyzed, and it was confirmed that the PCR caused no mutations.

Example 8

Transformation of *Aspergillus Niger* var. Macrosporus with PCN-Expression Vector pPTPCN and Expression of Recombinant PCN A transformation of *Aspergillus niger* var. macrosporus with PCN-expression vector pPTPCN was carried out by transforming a niaD-deficient strain of *Aspergillus niger* var. macrosporus using a niaD gene as a selective marker gene.

8-1) Isolation of niaD-Deficient Strain Nia2

Spores of *Aspergillus niger* var. macrosporus were applied on a Czapek medium-N (0.1% $K_2HPO_4$, 0.05% $MgSO_4.7H_2O$, 0.05% KCl, 0.001% $FeSO_4.2H_2O$, 3% sucrose, 1.5% purified agar, pH5.5-6.0) supplemented with 0.188% Na-glutamate and 3% $KClO_3$, and incubated at 30° C. for 5 to 7 days. Colonies were replicated to each medium in which the nitrogen source of the Czapek medium was replaced with $NO_3$, $NH_4$, or Glutamate, and incubated at 30° C. for 5 to 7 days. Among the replicated colonies, a strain which could grow on the medium containing $NH_4$ or Glutamate as the nitrogen source, but could not grow on the medium containing $NO_3$ as the nitrogen source was isolated as a niaD-deficient strain Nia2.

8-2) Isolation of Selection Marker Gene, niaD Gene

A PCR using the following primers Nia-N and Nia-C, designed on the basis of the 5'- and 3'-termini of the coding region of a niaD gene of Aspergillus niger reported by Uncle et al. [Uncle, S. E., Cambell, E. I., Punt, P. J., Hawker, K. L., Contreras, R., Hawkins, A. R., Van Den Hondel, C. A. and Kinghorn, J. R., "The *Aspergillus niger* niaD gene encoding nitrate reductase:upstream nucleotide and amino acid sequence comparisons", Gene 111(2), 149-155(1992)], was carried out to amplify the coding region of a niaD gene of *Aspergillus niger* var. macrosporus.

```
Nia-N:    ATGGCGACTGTCACTGAGGTG    (SEQ ID NO.: 22)

Nia-C:    TTAGAAGAAATGAAGGTCCGA    (SEQ ID NO.: 23)
```

The PCR was carried out using genomic DNA of *Aspergillus niger* var. macrosporus and an LA PCR™ KIT Ver2.1 (manufactured by Takara Bio). In the PCR, after a reaction at 94° C. for 1 minute, a cycle composed of a reaction at 94° C. for 30 seconds, a reaction at 55° C. for 30 seconds, and a reaction at 72° C. for 3 minutes was repeated 30 times, and a reaction at 72° C. for 7 minutes was carried out. As a result, a DNA fragment of approximately 3 kb was amplified. The amplified DNA fragment was labeled using an ECL direct system (manufactured by Amersham Pharmacia Biotech) as a probe.

The coding region of the niaD gene prepared by the above method was used as a probe to isolate a clone containing the promoter and terminator regions of the niaD gene from the genomic DNA library, which was prepared by the method described in Example 7-1, of *Aspergillus niger* var. macrosporus. In a fashion substantially similar to that described in Example 7, the genomic DNA library was screened to obtain a positive clone. The obtained phage clone was analyzed by Southern blotting in a fashion substantially similar to that described in Example 7. As a result, an XbaI-digested fragment of approximately 6.5 kb showed common hybridization patterns to those of chromosomal DNA. This XbaI fragment was cloned into the XbaI recognition sequence site of pUC118 to obtain plasmid pPTnia118. The nucleotide sequence of the obtained plasmid was analyzed to determine the nucleotide sequence of 6416 by (SEQ ID NO.: 24) containing the promoter and terminator regions of the niaD gene.

8-3) Introduction of PCN Gene into *Aspergillus Niger* var. Macrosporus Nia2 Strain The *Aspergillus niger* var. macrosporus Nia2 strain was cultivated in an S medium (3.0% glucose, 0.1% polypeptone, 1% yeast extract, 0.14% ammonium sulfate, 0.2% potassium phosphate, 0.03% magnesium sulfate, pH6.8) at 30° C. for 24 hours, and centrifuged at 3500 rpm for 10 minutes to collect the cells. The collected cells were washed with 0.5 mol/L sucrose, and suspended in an enzyme solution for preparing protoplasts (10 mg/mL β-glucuronidase, 3 mg/mL chitinase, 3 mg/mL zymolase, 0.5 mol/L sucrose), which had been filtrated through a 0.45 μm filter. The suspended mycelia was incubated at 30° C. for 60 minutes with shaking to prepare protoplasts. The suspension was filtrated through absorbent cotton, and centrifuged at 2500 rpm for 10 minutes to collect the protoplasts. The protoplasts were washed with an SUTC buffer (17.1% sucrose, 10 mmol/L Tris-HCl pH7.5, 10 mmol/L $CaCl_2$), and resuspended in 100 μL of the SUTC buffer. To the protoplast suspension, 7.5 μL of pPTPCN (1 μg/μL) and 2.5 μL of pPTnia118 (1 μg/μL) were added, and the mixture was allowed to stand on ice for 5 minutes. Further, 400 μL of a PEG solution (60% PEG4000, 10 mmol/L Tris-HCl pH7.5, 10 mmol/L $CaCl_2$) was added, and allowed to stand on ice for 20 minutes. After 10 mL of the SUTC buffer was further added, the whole was centrifuged at 2500 rpm for 10 minutes. The centrifuged protoplasts were suspended in 1 mL of the SUTC buffer, centrifuged at 4000 rpm for 5 minutes, and finally suspended in 100 μL of the SUTC buffer.

The resulting protoplasts were overlaid with soft agar on a modified Czapek medium (0.085% $NaNO_3$, 0.1% $K_2HPO_4$, 0.05% $MgSO_4.7H_2O$, 0.05% KCl, 0.001% $FeSO_4.2H_2O$, 17.1% sucrose, 1.5% purified agar, pH5.5-6.0), and incubated at 30° C. for 5 to 7 days. Colonies formed after the incubation was regarded as transformants.

8-4) PCN Expression and Measurement of Enzymatic Activity in Transformant of *Aspergillus Niger* var. Macrosporus Nia2 Strain The obtained transformants were cultivated in a P medium (1.0% starch, 6.0% soybean meal, 1.0% corn steep liquor, 0.3% ammonium sulfate, and 1% calcium carbonate) at 28° C. for 6 days. A supernatant of each culture was analyzed by SDS-PAGE to obtain a strain (No. 16) in which the band having a molecular weight of approximately 80 kDa, corresponding to the recombinant PCN, was observed. With respect to the culture supernatant of strain No. 16, and a supernatant obtained by similarly cultivating the Nia2 strain, the catalase activity was measured by the method described in Example 1. As shown in Table 1, the activity of strain No. 16 was 77 times or more that of the wild type, and it was confirmed that the recombinant PCN was expressed in strain No. 16.

TABLE 1

|  | Catalase activity (u/mL) |
|---|---|
| Wild type | less than 300 u/mL |
| Strain No. 16 | 23300 u/mL |

In this regard, "1 unit" of the catalase activity was regarded as the amount of the enzyme capable of decomposing 1 μmol of hydrogen peroxide per minute. Further, the catalase activity of the culture supernatant of *Penicillium pinophilum* prepared by the method described in Example 1 was 385 U/mL. This result shows that the productivity of PCN remarkably increases by expressing PCN in *Aspergillus niger* var. macrosporus as a host.

8-5) Analysis of N-Terminal Amino Acid Sequence

The culture supernatant of the transformant No. 16 strain obtained in Example 8-4 was subjected to SDS-PAGE, and separated proteins were transferred to a PVDF membrane Immobilon-PSQ (manufactured by Millipore). The PVDF membrane was stained with Coomassie brilliant blue. A portion in which the protein of approximately 80 kDa was blotted was cut from the membrane, and subjected to an amino acid sequencer model 492 to determine the amino acid sequence of 11 residues at the amino-terminus. The amino sequence was as follows:

```
DDSNASSETEA    (Amino acids 1-11 of SEQ ID NO.: 5)
```

This amino acid sequence was identical with the N-terminal amino acid of PCN derived from *Penicillium pinophilum*, and thus, it was confirmed that the protein of approximately 80 kDa was the recombinant PCN.

8-6) Evaluation of Thermostability in Recombinant PCN

As described in Example 1, the thermostability of naturally-occurring PCN produced by *Penicillium pinophilum* was 50%. The thermostability of the recombinant PCN obtained by the method described in Example 8-4 was evaluated by the method described in Example 1. As a result, the thermostability was 71.3%. This result revealed that the thermostability of the recombinant PCN was remarkably improved in comparison with that of naturally-occurring PCN.

Although the present invention has been described with reference to specific embodiments, various changes and modifications obvious to those skilled in the art are possible without departing from the scope of the appended claims.

Free Text in Sequence Listing

The nucleotide sequences of SEQ ID NOS.: 6-9 and 11-14 are artificially synthesized primer sequences, i.e., P catalase F (SEQ ID NO.: 6), P catalase R (SEQ ID NO.: 7), PCNF (SEQ ID NO.: 8), PCNR (SEQ ID NO.: 9), H catalase F (SEQ ID NO.: 11), H catalase R (SEQ ID NO.: 12), HCNF (SEQ ID NO.: 13), HCNR (SEQ ID NO.: 14), proctaseB-N (SEQ ID NO.: 15), proctaseB-C (SEQ ID NO.: 16), proctaseBNxba (SEQ ID NO.: 17), proctaseBCxba (SEQ ID NO.: 18), PCN-XbaIPtN (SEQ ID NO.: 19), PCN-XbaIPtC (SEQ ID NO.: 20), and Nia-N (SEQ ID NO.: 22), and Nia-C (SEQ ID NO.: 23), respectively.

The nucleotide sequence of ID NO.: 21 is plasmid pPT-PCN.

The abbreviations "N" at the 18th position of SEQ ID NO.: 6, the 3rd, 6th, and 12th positions of SEQ ID NO.: 11, and the 6th and 9th positions of SEQ ID NO.: 12 stand for an arbitrary nucleotide; and the abbreviation "N" at the 12th position of SEQ ID NO.: 12 stands for deoxyinosine.

The invention claimed is:

1. An isolated thermostable catalase produced by *Penicillium pinophilum*, selected from the group consisting of:
   (i) a protein comprising the amino acid sequence consisting of amino acids 1-692 of SEQ ID NO: 2;
   (ii) a protein comprising an amino acid sequence in which one to twenty amino acids are deleted, substituted, or added in the amino acid sequence consisting of amino acids 1-692 of SEQ ID NO: 2, and having a thermostable catalase activity;
   (iii) a protein comprising an amino acid sequence having 90% or more identity with the amino acid sequence of a protein consisting of amino acids 1-692 of SEQ ID NO:2, and having a thermostable catalase activity;
   (iv) a protein consisting of the amino acid sequence consisting of amino acids 1-692 of SEQ ID NO:2, and having a thermostable catalase activity; and
   (v) the proteins (i) to (iv), having the amino acid sequence consisting of amino acids -1 to -42 of SEQ ID NO: 2, or an amino acid sequence in which one or two amino acids are deleted, substituted, or added in the amino acid sequence consisting of amino acids -1 to -42 of SEQ ID NO:2, at the N-terminal side of the protein.

2. The thermostable catalase according to claim 1, having a molecular weight of approximately 80 kDa.

3. An isolated protein selected from the group consisting of:
   (i) a protein comprising the amino acid sequence consisting of amino acids 1-692 of SEQ ID NO.: 2;
   (ii) a protein comprising an amino acid sequence in which one to twenty amino acids are deleted, substituted, or added in the amino acid sequence consisting of amino acids 1-692 of SEQ ID NO.: 2, and having a thermostable catalase activity;
   (iii) a protein comprising an amino acid sequence having 90% or more identity with the amino acid sequence of a protein consisting of amino acids 1-692 of SEQ ID NO.: 2, and having a thermostable catalase activity;
   (iv) a protein consisting of the amino acid sequence consisting of amino acids 1-692 of SEQ ID NO.: 2, and having a thermostable catalase activity; and
   (v) the proteins (i) to (iv), having the amino acid sequence consisting of amino acids -1 to -42 of SEQ ID NO.: 2, or an amino acid sequence in which one or two amino acids are deleted, substituted, or added in the amino acid sequence consisting of amino acids - 1 to - 42 of SEQ ID NO.: 2, at the N-terminal side of the protein.

\* \* \* \* \*

SEQUENCE LISTING

```
<160> NUMBER OF SEQ ID NOS: 24

<210> SEQ ID NO 1
<211> LENGTH: 2403
<212> TYPE: DNA
<213> ORGANISM: Artificial Sequence
<220> FEATURE:
<223> OTHER INFORMATION: Penicillum pinophilum

<400> SEQUENCE: 1
atgcgaggat tatactccct cggcgccttc gccagtctca ttgcggcggc ttcggctgca      60
tgcccaatgc tgactggcga aatcccagct ggtagtgttg ccaatcctca tcatcacgga     120
aagcgtgacg attcaaatgc ttcctccgaa acagaagcct ttctgtccga gttctacctc     180
aacgacaacg atgcctatct caccaccgat gtaggcggtc cgatcgagga tcaaaacagt     240
ttgaaggccg gcattcgtgg atcgaccctc ttggaagact tcatcttccg tcagaaaatc     300
cagcattttg atcatgagcg tgtaggttat ccattctatc acgtacttca ggggtagttc     360
tgacatgccc aggtcccgga acgtgccgtg catgctcgag gtgcaggtgc tcatggtgta     420
tttacttcat atgccgactg gtccaacatc actgctgctt catttttggg agcttccgga     480
aaggaaacgc ccacatttgt ccgcttctcg actgttgcag gcagccgagg aagtgccgac     540
accgctcgtg acgttcacgg atttgctact cgcttctata ctgacgaggg aaactatggt     600
agcctttctc tttgactcgt ccatagatag ggatgtaact gacttcaaca gacattgttg     660
gaaacaacat tcctgtcttc ttcatccaag atgctatctt attcccagat ctcatccata     720
gcgttaagcc acagccagcc aatgaaatcc cacaggctgc tactgcacac gacacggcct     780
atgacttctt tggtcaacag ccaagcactc tgcataccct cttctgggca atggcaggcc     840
atggtatccc acggtctttc cgtcatgttg acggattcgg tgtccacacc tatcggttcg     900
tgacagatga tggctcgtcc aagttggtca aatttcactg gacatcgctg caaggtcggg     960
ccagtctggt ctgggaggaa gctcaggcca ctgctggcaa aaatgccgac tttatgagac    1020
aggatctgta tgatagcatt gaggctggcc gttatccaga gtgggaggta tgtaccaccg    1080
aattcatgga aagtactcga ctaacgtgaa cagctcggcg tgcaaataat tgaggagtcg    1140
gatgtcttaa gctacggatt tgacctgttg gatccaacca agattcttcc ggttgaaaaa    1200
gttccaatta ctgcgctcgg aaaaatgcaa ctcaaccgta atccattgaa ttactttgcc    1260
gagacagagc aagtcatggt aagtcgacct tccggcactc gagtcatttc ctactaacgt    1320
ggatagttcc aacctggcca cattgttcgt ggtatcgact tcacctatta tcctcttctc    1380
cagggtcgtt tattctccta cctcgatact cagctgaatc gcaatggtgg tcccaacttt    1440
gaacaaattc caatcaatcg tccgcgtgtt cctatccaca caacaaccg cgatggattc    1500 gcccaaatgt ttattccttt gaaccaggca gcatattcac ccaacacctt gaataatggc    1560
tctcctcgac aagccaacga gactgtcgga aatggcttct ttaccgcccc cgggcgctcc    1620
```

```
gcagatggac accttgttcg cgctacgagc ccaacatttg ccgacgtgtg gtctcagcct   1680
ggcttgtttt acaactcctt gacggctacc gaacaacagt tcgtgatcaa tgctttgcgt   1740
ttcgaattgt ctaatgtaaa gagcgaggat gttaaaagca atttcatcac acagataaat   1800
cgcgtaaaca acacgttagc aacacttgtg gcttctgcaa ttggagtctc cgcgcccgaa   1860
cccgactcta catactacca cagcaataag acgtctaatg tcggaacatt cggtactccg   1920
ttgaaaaagc ttgacggtct caaggtcgga gtccttgctt cggtgaacgg tgaaagtagt   1980
attgccgagg acaagcatt ggcacaaagc ctagcgggct cgaacgtgga cgtcgttatc   2040
gtcgccgagc atcttacttc gaacgtgtca gctacatact ctggatcaga cgcaacgaac   2100
tttgatgctg ttattgtcag ctcaggggct gaaggtctct ttggacctca aacctttaca   2160
gccgaatcca atacaacact ttatccggca ggccgtccta gccagatttt ggtcgatgcc   2220
ttccgctttg gcaagccggt tggagcagtt ggtggtgcca gtgcagctct gtcagcggtg   2280
gatatcagta ctgatcgtag tggtgtgatt actggtgatt ccgtcagtga cgactttgtc   2340
aagcagctaa cggaggacct tgccacattc aaattcttgg accgattcgc tgtggatgag   2400
tag                                                                 2403
```

<210> SEQ ID NO 2
<211> LENGTH: 734
<212> TYPE: PRT
<213> ORGANISM: Artificial Sequence
<220> FEATURE:
<223> OTHER INFORMATION: Penicillium pinophilum

<400> SEQUENCE: 2

```
Met Arg Gly Leu Tyr Ser Leu Gly Ala Phe Ala Ser Leu Ile Ala Ala
1               5                   10                  15

Ala Ser Ala Ala Cys Pro Met Leu Thr Gly Glu Ile Pro Ala Gly Ser
            20                  25                  30

Val Ala Asn Pro His His His Gly Lys Arg Asp Asp Ser Asn Ala Ser
        35                  40                  45

Ser Glu Thr Glu Ala Phe Leu Ser Glu Phe Tyr Leu Asn Asp Asn Asp
    50                  55                  60

Ala Tyr Leu Thr Thr Asp Val Gly Gly Pro Ile Glu Asp Gln Asn Ser
65                  70                  75                  80

Leu Lys Ala Gly Ile Arg Gly Ser Thr Leu Leu Glu Asp Phe Ile Phe
                85                  90                  95

Arg Gln Lys Ile Gln His Phe Asp His Glu Arg Val Pro Glu Arg Ala
            100                 105                 110

Val His Ala Arg Gly Ala Gly Ala His Gly Val Phe Thr Ser Tyr Ala
        115                 120                 125

Asp Trp Ser Asn Ile Thr Ala Ala Ser Phe Leu Gly Ala Ser Gly Lys
    130                 135                 140

Glu Thr Pro Thr Phe Val Arg Phe Ser Thr Val Ala Gly Ser Arg Gly
145                 150                 155                 160

Ser Ala Asp Thr Ala Arg Asp Val His Gly Phe Ala Thr Arg Phe Tyr
                165                 170                 175

Thr Asp Glu Gly Asn Tyr Asp Ile Val Gly Asn Asn Ile Pro Val Phe
            180                 185                 190

Phe Ile Gln Asp Ala Ile Leu Phe Pro Asp Leu Ile His Ser Val Lys
        195                 200                 205

Pro Gln Pro Ala Asn Glu Ile Pro Gln Ala Ala Thr Ala His Asp Thr
    210                 215                 220
```

```
Ala Tyr Asp Phe Phe Gly Gln Gln Pro Ser Thr Leu His Thr Leu Phe
225                 230                 235                 240

Trp Ala Met Ala Gly His Gly Ile Pro Arg Ser Phe Arg His Val Asp
            245                 250                 255

Gly Phe Gly Val His Thr Tyr Arg Phe Val Thr Asp Asp Gly Ser Ser
                260                 265                 270

Lys Leu Val Lys Phe His Trp Thr Ser Leu Gln Gly Arg Ala Ser Leu
            275                 280                 285

Val Trp Glu Glu Ala Gln Ala Thr Ala Gly Lys Asn Ala Asp Phe Met
        290                 295                 300

Arg Gln Asp Leu Tyr Asp Ser Ile Glu Ala Gly Arg Tyr Pro Glu Trp
305                 310                 315                 320

Glu Leu Gly Val Gln Ile Ile Glu Glu Ser Asp Val Leu Ser Tyr Gly
                325                 330                 335

Phe Asp Leu Leu Asp Pro Thr Lys Ile Leu Pro Val Glu Lys Val Pro
            340                 345                 350

Ile Thr Ala Leu Gly Lys Met Gln Leu Asn Arg Asn Pro Leu Asn Tyr
        355                 360                 365

Phe Ala Glu Thr Glu Gln Val Met Phe Gln Pro Gly His Ile Val Arg
370                 375                 380

Gly Ile Asp Phe Thr Tyr Tyr Pro Leu Leu Gln Gly Arg Leu Phe Ser
385                 390                 395                 400

Tyr Leu Asp Thr Gln Leu Asn Arg Asn Gly Gly Pro Asn Phe Glu Gln
                405                 410                 415

Ile Pro Ile Asn Arg Pro Arg Val Pro Ile His Asn Asn Arg Asp
            420                 425                 430

Gly Phe Ala Gln Met Phe Ile Pro Leu Asn Gln Ala Ala Tyr Ser Pro
        435                 440                 445

Asn Thr Leu Asn Asn Gly Ser Pro Arg Gln Ala Asn Glu Thr Val Gly
450                 455                 460

Asn Gly Phe Phe Thr Ala Pro Gly Arg Ser Ala Asp Gly His Leu Val
465                 470                 475                 480

Arg Ala Thr Ser Pro Thr Phe Ala Asp Val Trp Ser Gln Pro Gly Leu
                485                 490                 495

Phe Tyr Asn Ser Leu Thr Ala Thr Glu Gln Gln Phe Val Ile Asn Ala
            500                 505                 510

Leu Arg Phe Glu Leu Ser Asn Val Lys Ser Glu Asp Val Lys Ser Asn
        515                 520                 525

Phe Ile Thr Gln Ile Asn Arg Val Asn Asn Thr Leu Ala Thr Leu Val
530                 535                 540

Ala Ser Ala Ile Gly Val Ser Ala Pro Glu Pro Asp Ser Thr Tyr Tyr
545                 550                 555                 560

His Ser Asn Lys Thr Ser Asn Val Gly Thr Phe Gly Thr Pro Leu Lys
                565                 570                 575

Lys Leu Asp Gly Leu Lys Val Gly Val Leu Ala Ser Val Asn Gly Glu
            580                 585                 590

Ser Ser Ile Ala Glu Gly Gln Ala Leu Ala Gln Ser Leu Ala Gly Ser
        595                 600                 605

Asn Val Asp Val Val Ile Val Ala Glu His Leu Thr Ser Asn Val Ser
610                 615                 620

Ala Thr Tyr Ser Gly Ser Asp Ala Thr Asn Phe Asp Ala Val Ile Val
625                 630                 635                 640
```

Ser Ser Gly Ala Glu Gly Leu Phe Gly Pro Gln Thr Phe Thr Ala Glu
            645                 650                 655

Ser Asn Thr Thr Leu Tyr Pro Ala Gly Arg Pro Ser Gln Ile Leu Val
        660                 665                 670

Asp Ala Phe Arg Phe Gly Lys Pro Val Gly Ala Val Gly Gly Ala Ser
    675                 680                 685

Ala Ala Leu Ser Ala Val Asp Ile Ser Thr Asp Arg Ser Gly Val Ile
690                 695                 700

Thr Gly Asp Ser Val Ser Asp Asp Phe Val Lys Gln Leu Thr Glu Asp
705                 710                 715                 720

Leu Ala Thr Phe Lys Phe Leu Asp Arg Phe Ala Val Asp Glu
                725                 730

<210> SEQ ID NO 3
<211> LENGTH: 2749
<212> TYPE: DNA
<213> ORGANISM: Artificial Sequence
<220> FEATURE:
<223> OTHER INFORMATION: Humicola grisea

<400> SEQUENCE: 3

| | | | | | |
|---|---|---|---|---|---|
| atgaacagag | tcacgaatct | cctcgcctgg | gccggcgcga | tagggctcgc | ccaagcaaca | 60 |
| tgccccttcg | cggaccctgc | cgctctgtat | aggcgtcagg | atactaccag | cggccagtcg | 120 |
| ccacttgcag | catacgaggt | ggatgacagc | accggatacc | tgacctccga | tgttggcggg | 180 |
| cccattcagg | accagaccag | cctcaaggca | ggcatccggg | gtccgaccct | tcttgaggac | 240 |
| tttatgttcc | gccagaagat | ccagcacttc | gaccatgaac | gggtaaggac | ataatgctca | 300 |
| cacgagcggc | tgcgtaccta | tttattttga | acgggtaagg | acataatgct | cacacgagcg | 360 |
| gctgcgtacc | tatttatttc | gagagatgg | gctggctggc | tggctgtgat | gcctgagttt | 420 |
| ggggacatac | ggagtacctt | actgacgcgc | taatccactc | caggttcccg | aaagggcggt | 480 |
| ccatgctcga | ggcgctggag | cacacgggac | cttcacgagt | tacgccgact | ggagtaacat | 540 |
| caccgcggcg | tcctttctga | acgccacagg | aaagcagacg | ccggtgtttg | tccggttctc | 600 |
| gaccgttgct | gggtctcgag | ggagcgcaga | cacggcgaga | cgttcatg | gtttcgcgac | 660 |
| gcggttgtaa | gttttgttgt | gtttcattcg | ttccggtctg | tagaggaggg | ttaggatatg | 720 |
| agctaacgtg | tgtgtgtgtg | tgtgaagtta | cactgatgaa | ggcaactttg | gtacgtccca | 780 |
| cgcatggtcc | tcaattctct | tatctggcag | cgatgtggtc | attgtcgacg | ttgctaactt | 840 |
| gcgtagatat | cgtcggaaac | aacatcccgg | tattcttcat | tcaagatgca | atccagttcc | 900 |
| ctgaccttat | ccactcggtc | aagccgagtc | agacaacga | gattccccaa | gcggcgacgg | 960 |
| ctcatgattc | agcttgggac | ttcttcagcc | agcagccaag | cgccatggta | agcaatggac | 1020 |
| caaggagccg | cacctggggt | gacataccag | ggagtacacg | gggcgttccg | atgaccctcg | 1080 |
| tgtgaccaag | gcagtacaac | actccacgga | ggactcgaag | agattcggaa | atatggaaca | 1140 |
| cagaactgac | aggatggtag | cacacgttgt | tctgggccat | gtctggccac | ggaatccctc | 1200 |
| gcagctatcg | ccatatggta | cgtttgcctg | gctgagatga | ccgtgaatcc | atttctaacc | 1260 |
| tcaagtccag | gatggcttcg | gcgtccacac | gttccggttt | gtcaaagatg | acggctcgtc | 1320 |
| caagttgatc | aagtggcatt | tcaagtcacg | ccagggaaag | gcgagtctag | tctgggaaga | 1380 |
| ggcgcaggtt | ctttctggca | agaatgccga | cttccaccgt | caggacctct | gggatgctat | 1440 |
| tgagtccggg | aacggaccag | aatgggatgt | ctgcgtccag | attgtcgatg | agtcccaggc | 1500 |
| gcaagccttt | ggcttcgact | tgctggaccc | gacaaagatc | atccccgagg | agtacgcccc | 1560 |

```
cttgacgaaa ctggggctct tgaagctgga tcgcaatccg accaactact tcgccgagac   1620
ggagcaggtc atgttccaac ccggtcatat agtccgcggc gtcgacttca cggaggatcc   1680
cctgctacag ggacgtctct tctcgtacct tgacacgcag ctgaaccgga atggcgggcc   1740
caactttgag cagctgccca tcaacatgcc gcgggtgccg attcacaaca ataatcgcga   1800
cggcgccggc cagatgttca tccacaggaa caagtatcct tgtaagtacc tcttttgcct   1860
cgatcgttgt ggtgccggct tgctgacaga cgcagacact cccaacaccc tgaacagtgg   1920
ttatccgcgg caagccaacc aaaatgccgg acgcggattc ttcacagcgc tggccgtac    1980 cgtcagcggt gccctcgtcc gtgaggtgtc gccaacattc aacgaccact ggtcgcagcc   2040
ccgtctcttc ttcaactccc tcactcccgt cgaacagcag ttcctcgtca cgccatgcg    2100 cttcgaaatc agccttgtga agtcggaaga atgcaggaag aacgtgctca cccagctcaa   2160
ccgcgtcagc catgatgtgg ccgtgcgcgt ggccgccgct atcggcctcg ccgcgcccga   2220
cgcggacgac acatactacc acaacaacaa gacggctggc gtctcgatcc ttggaagcgg   2280
gcccttgcct accatcaaga ctctccgcgt cggcatcctg gctaccacga gcgagtcgag   2340
cgcgctggat caggcagccc agctccgcac ccgtctggaa aaggacgggc ttgtggtcac   2400
ggttgtggct gaaacgctgc gcgaggggt  agaccagaca tactcgacgg cggatgccac   2460
gggtttcgac ggcgttgttg ttgtggacgg ggcggcggcg ctgtttgcca gcaccgcgtc   2520
gtcgccgttg ttcccgacgg gcaggccgtt gcagatcttt gtggacgcgt atcggtgggg   2580
aaagccggtc ggtgtgtgtg gtgggaagtc gagcgaggtg ttggatgcgg cggatgttcc   2640
ggaaaatggg gacggggtgt attcggagga gtcggtggac aagtttgtgg aggagtttga   2700 gaagggggttg gctactttca gggtgagtct tggtgccttt gtttttttga              2749
```

<210> SEQ ID NO 4
<211> LENGTH: 716
<212> TYPE: PRT
<213> ORGANISM: Artificial Sequence
<220> FEATURE:
<223> OTHER INFORMATION: Humicola grisea

<400> SEQUENCE: 4

```
Met Asn Arg Val Thr Asn Leu Leu Ala Trp Ala Gly Ala Ile Gly Leu
1               5                   10                  15

Ala Gln Ala Thr Cys Pro Phe Ala Asp Pro Ala Ala Leu Tyr Arg Arg
            20                  25                  30

Gln Asp Thr Thr Ser Gly Gln Ser Pro Leu Ala Ala Tyr Glu Val Asp
        35                  40                  45

Asp Ser Thr Gly Tyr Leu Thr Ser Asp Val Gly Gly Pro Ile Gln Asp
    50                  55                  60

Gln Thr Ser Leu Lys Ala Gly Ile Arg Gly Pro Thr Leu Leu Glu Asp
65                  70                  75                  80

Phe Met Phe Arg Gln Lys Ile Gln His Phe Asp His Glu Arg Val Pro
                85                  90                  95

Glu Arg Ala Val His Ala Arg Gly Ala Gly Ala His Gly Thr Phe Thr
            100                 105                 110

Ser Tyr Ala Asp Trp Ser Asn Ile Thr Ala Ala Ser Phe Leu Asn Ala
        115                 120                 125

Thr Gly Lys Gln Thr Pro Val Phe Val Arg Phe Ser Thr Val Ala Gly
    130                 135                 140

Ser Arg Gly Ser Ala Asp Thr Ala Arg Asp Val His Gly Phe Ala Thr
```

```
            145                 150                 155                 160
        Arg Phe Tyr Thr Asp Glu Gly Asn Phe Asp Ile Val Gly Asn Asn Ile
                        165                 170                 175
        Pro Val Phe Phe Ile Gln Asp Ala Ile Gln Phe Pro Asp Leu Ile His
                        180                 185                 190
        Ser Val Lys Pro Ser Pro Asp Asn Glu Ile Pro Gln Ala Ala Thr Ala
                        195                 200                 205
        His Asp Ser Ala Trp Asp Phe Phe Ser Gln Pro Ser Ala Met His
                        210                 215                 220
        Thr Leu Phe Trp Ala Met Ser Gly His Gly Ile Pro Arg Ser Tyr Arg
        225                 230                 235                 240
        His Met Asp Gly Phe Gly Val His Thr Phe Arg Phe Val Lys Asp Asp
                        245                 250                 255
        Gly Ser Ser Lys Leu Ile Lys Trp His Phe Lys Ser Arg Gln Gly Lys
                        260                 265                 270
        Ala Ser Leu Val Trp Glu Glu Ala Gln Val Leu Ser Gly Lys Asn Ala
                        275                 280                 285
        Asp Phe His Arg Gln Asp Leu Trp Asp Ala Ile Glu Ser Gly Asn Gly
                        290                 295                 300
        Pro Glu Trp Asp Val Cys Val Gln Ile Val Asp Glu Ser Gln Ala Gln
        305                 310                 315                 320
        Ala Phe Gly Phe Asp Leu Leu Asp Pro Thr Lys Ile Ile Pro Glu Glu
                        325                 330                 335
        Tyr Ala Pro Leu Thr Lys Leu Gly Leu Leu Lys Leu Asp Arg Asn Pro
                        340                 345                 350
        Thr Asn Tyr Phe Ala Glu Thr Glu Gln Val Met Phe Gln Pro Gly His
                        355                 360                 365
        Ile Val Arg Gly Val Asp Phe Thr Glu Asp Pro Leu Leu Gln Gly Arg
                        370                 375                 380
        Leu Phe Ser Tyr Leu Asp Thr Gln Leu Asn Arg Asn Gly Gly Pro Asn
        385                 390                 395                 400
        Phe Glu Gln Leu Pro Ile Asn Met Pro Arg Val Pro Ile His Asn Asn
                        405                 410                 415
        Asn Arg Asp Gly Ala Gly Gln Met Phe Ile His Arg Asn Lys Tyr Pro
                        420                 425                 430
        Tyr Thr Pro Asn Thr Leu Asn Ser Gly Tyr Pro Arg Gln Ala Asn Gln
                        435                 440                 445
        Asn Ala Gly Arg Gly Phe Phe Thr Ala Pro Gly Arg Thr Val Ser Gly
        450                 455                 460
        Ala Leu Val Arg Glu Val Ser Pro Thr Phe Asn Asp His Trp Ser Gln
        465                 470                 475                 480
        Pro Arg Leu Phe Phe Asn Ser Leu Thr Pro Val Glu Gln Gln Phe Leu
                        485                 490                 495
        Val Asn Ala Met Arg Phe Glu Ile Ser Leu Val Lys Ser Glu Glu Cys
                        500                 505                 510
        Arg Lys Asn Val Leu Thr Gln Leu Asn Arg Val Ser His Asp Val Ala
                        515                 520                 525
        Val Arg Val Ala Ala Ile Gly Leu Ala Ala Pro Asp Ala Asp Asp
        530                 535                 540
        Thr Tyr Tyr His Asn Asn Lys Thr Ala Gly Val Ser Ile Leu Gly Ser
        545                 550                 555                 560
        Gly Pro Leu Pro Thr Ile Lys Thr Leu Arg Val Gly Ile Leu Ala Thr
                        565                 570                 575
```

```
Thr Ser Glu Ser Ser Ala Leu Asp Gln Ala Ala Gln Leu Arg Thr Arg
            580                 585                 590

Leu Glu Lys Asp Gly Leu Val Val Thr Val Ala Glu Thr Leu Arg
        595                 600                 605

Glu Gly Val Asp Gln Thr Tyr Ser Thr Ala Asp Ala Thr Gly Phe Asp
610                 615                 620

Gly Val Val Val Asp Gly Ala Ala Ala Leu Phe Ala Ser Thr Ala
625                 630                 635                 640

Ser Ser Pro Leu Phe Pro Thr Gly Arg Pro Leu Gln Ile Phe Val Asp
                645                 650                 655

Ala Tyr Arg Trp Gly Lys Pro Val Gly Val Cys Gly Gly Lys Ser Ser
            660                 665                 670

Glu Val Leu Asp Ala Ala Asp Val Pro Glu Asn Gly Asp Gly Val Tyr
        675                 680                 685

Ser Glu Glu Ser Val Asp Lys Phe Val Glu Glu Phe Glu Lys Gly Leu
            690                 695                 700

Ala Thr Phe Arg Val Ser Leu Gly Ala Phe Val Phe
705                 710                 715
```

```
<210> SEQ ID NO 5
<211> LENGTH: 31
<212> TYPE: PRT
<213> ORGANISM: Artificial Sequence
<220> FEATURE:
<223> OTHER INFORMATION: Penicillum pinophilum

<400> SEQUENCE: 5

Asp Asp Ser Asn Ala Ser Ser Glu Thr Glu Ala Phe Leu Ser Glu Phe
1               5                   10                  15

Tyr Leu Asn Asp Asn Asp Ala Tyr Leu Thr Thr Asp Val Gly Gly
            20                  25                  30

<210> SEQ ID NO 6
<211> LENGTH: 26
<212> TYPE: DNA
<213> ORGANISM: Artificial Sequence
<220> FEATURE:
<223> OTHER INFORMATION: primer: P catalase F
<220> FEATURE:
<221> NAME/KEY: misc_feature
<222> LOCATION: (18)..(18)
<223> OTHER INFORMATION: a, g, c, or t or other
<220> FEATURE:
<221> NAME/KEY: misc_feature
<222> LOCATION: (21)..(21)
<223> OTHER INFORMATION: g or a
<220> FEATURE:
<221> NAME/KEY: misc_feature
<222> LOCATION: (25)..(25)
<223> OTHER INFORMATION: g or a

<400> SEQUENCE: 6
gaggccggca actacccnga rtggra                                    26

<210> SEQ ID NO 7
<211> LENGTH: 25
<212> TYPE: DNA
<213> ORGANISM: Artificial Sequence
<220> FEATURE:
<223> OTHER INFORMATION: primer: P catalase R
<220> FEATURE:
<221> NAME/KEY: misc_feature
<222> LOCATION: (17)..(17)
<223> OTHER INFORMATION: g or a
```

-continued

```
<220> FEATURE:
<221> NAME/KEY: misc_feature
<222> LOCATION: (20)..(20)
<223> OTHER INFORMATION: g or a
<220> FEATURE:
<221> NAME/KEY: misc_feature
<222> LOCATION: (21)..(21)
<223> OTHER INFORMATION: a or t
<220> FEATURE:
<221> NAME/KEY: misc_feature
<222> LOCATION: (23)..(23)
<223> OTHER INFORMATION: g or a

<400> SEQUENCE: 7
cctgctcggt ctcggcraar wartt                                          25

<210> SEQ ID NO 8
<211> LENGTH: 21
<212> TYPE: DNA
<213> ORGANISM: Artificial Sequence
<220> FEATURE:
<223> OTHER INFORMATION: primer: PCNF

<400> SEQUENCE: 8
atgcgaggat tatactccct c                                              21

<210> SEQ ID NO 9
<211> LENGTH: 21
<212> TYPE: DNA
<213> ORGANISM: Artificial Sequence
<220> FEATURE:
<223> OTHER INFORMATION: primer: PCNR

<400> SEQUENCE: 9
ctactcatcc acagcgaatc g                                              21

<210> SEQ ID NO 10
<211> LENGTH: 20
<212> TYPE: PRT
<213> ORGANISM: Artificial Sequence
<220> FEATURE:
<223> OTHER INFORMATION: Humicola grisea

<400> SEQUENCE: 10

Gln Asp Thr Thr Ser Gly Gln Ser Pro Leu Ala Ala Tyr Glu Val Asp
1               5                   10                  15

Asp Ser Thr Gly
            20

<210> SEQ ID NO 11
<211> LENGTH: 17
<212> TYPE: DNA
<213> ORGANISM: Artificial Sequence
<220> FEATURE:
<223> OTHER INFORMATION: primer: H catalase F
<220> FEATURE:
<221> NAME/KEY: misc_feature
<222> LOCATION: (3)..(3)
<223> OTHER INFORMATION: a, g, c, or t or other
<220> FEATURE:
<221> NAME/KEY: misc_feature
<222> LOCATION: (6)..(6)
<223> OTHER INFORMATION: a, g, c, or t or other
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (12)..(12)
```

<223> OTHER INFORMATION: a, g, c, or t or other

<400> SEQUENCE: 11
gtncgnttyt cnactgt                                                                                          17

<210> SEQ ID NO 12
<211> LENGTH: 20
<212> TYPE: DNA
<213> ORGANISM: Artificial Sequence
<220> FEATURE:
<223> OTHER INFORMATION: primer: H catalase R
<220> FEATURE:
<221> NAME/KEY: misc_feature
<222> LOCATION: (3)..(3)
<223> OTHER INFORMATION: g or a
<220> FEATURE:
<221> NAME/KEY: misc_feature
<222> LOCATION: (6)..(6)
<223> OTHER INFORMATION: a, g, c, or t or other
<220> FEATURE:
<221> NAME/KEY: misc_feature
<222> LOCATION: (9)..(9)
<223> OTHER INFORMATION: a, g, c, or t or other
<220> FEATURE:
<221> NAME/KEY: misc_feature
<222> LOCATION: (12)..(12)
<223> OTHER INFORMATION: deoxyinosine
<220> FEATURE:
<221> NAME/KEY: misc_feature
<222> LOCATION: (15)..(15)
<223> OTHER INFORMATION: g or a

<400> SEQUENCE: 12
aaraanacng gnttrttgtt                                                                                       20

<210> SEQ ID NO 13
<211> LENGTH: 21
<212> TYPE: DNA
<213> ORGANISM: Artificial Sequence
<220> FEATURE:
<223> OTHER INFORMATION: primer: HCNF

<400> SEQUENCE: 13
atgaacagag tcacgaatct c                                                                                     21

<210> SEQ ID NO 14
<211> LENGTH: 21
<212> TYPE: DNA
<213> ORGANISM: Artificial Sequence
<220> FEATURE:
<223> OTHER INFORMATION: primer: HCNR

<400> SEQUENCE: 14
tcaaaaaaca aaggcaccaa g                                                                                     21

<210> SEQ ID NO 15
<211> LENGTH: 21
<212> TYPE: DNA
<213> ORGANISM: Artificial Sequence
<220> FEATURE:
<223> OTHER INFORMATION: primer: proctaseB-N

<400> SEQUENCE: 15
atggtcgtct tcagcaaaac c                                                                                     21

<210> SEQ ID NO 16
<211> LENGTH: 21
<212> TYPE: DNA
<213> ORGANISM: Artificial Sequence
<220> FEATURE:
<223> OTHER INFORMATION: primer: proctaseB-C

<400> SEQUENCE: 16
ctaagcctga gcggcgaatc c                                             21

<210> SEQ ID NO 17
<211> LENGTH: 25
<212> TYPE: DNA
<213> ORGANISM: Artificial Sequence
<220> FEATURE:
<223> OTHER INFORMATION: primer: proctaseBNxba

<400> SEQUENCE: 17
ggtctagaat gtcaagcaag agagt                                         25

<210> SEQ ID NO 18
<211> LENGTH: 26
<212> TYPE: DNA
<213> ORGANISM: Artificial Sequence
<220> FEATURE:
<223> OTHER INFORMATION: primer: proctaseBCxba

<400> SEQUENCE: 18
ggtctagaat caaccactga agtgga                                        26

<210> SEQ ID NO 19
<211> LENGTH: 35
<212> TYPE: DNA
<213> ORGANISM: Artificial Sequence
<220> FEATURE:
<223> OTHER INFORMATION: primer: PCN-XbaIPtN

<400> SEQUENCE: 19
ggtctagagg tcaaaatgcg aggattatac tccct                              35

<210> SEQ ID NO 20
<211> LENGTH: 30
<212> TYPE: DNA
<213> ORGANISM: Artificial Sequence
<220> FEATURE:
<223> OTHER INFORMATION: primer : PCN-XbaIPtC

<400> SEQUENCE: 20
ggtctagact actcatccac agcgaatcgg                                    30

<210> SEQ ID NO 21
<211> LENGTH: 9728
<212> TYPE: DNA
<213> ORGANISM: Artificial Sequence
<220> FEATURE:
<223> OTHER INFORMATION: plasmid pPTPCN

<400> SEQUENCE: 21
tcgagattct ggtcccgcgc gaccacctca agcatgcccc tgtccggacg tgctttcgta    60
ttctgtcggg gatgattttc atcttgaagg taggcccctt cggttccccc gtaggccgtg   120
gctctgctga caatttttcca gactttcacg ctcggtgcca agaagacga tgtgcgtgtg   180 tcgctggacc tccaggatcg caccattgaa gccttgaaga cctgcgtagt cgacgatgtt   240
cacctaaacc acgcgattgc gcgattgttg gaattgctca ccaccagcat tcgcacgcgt   300
tttctgcgtt tcgcgccctt ggaccgcagc ggcgatggcg aacaagaacg cccatccgca   360
ccagtctcac ggcatcagtc gccgcggccg cgtgaagggc cacaaaaccg ccgggaaggg   420

```
tcggcgcatg cctggacgcc agcgcagagt gcgacacaaa atctgggata tgtcgatagc    480
aatagccaga cggggaccag catgacttct gtccatgatc cgctggccgg catccctgcc    540
cagccgatca attcgtccaa catcaatgtc tcgttcatgc ccctcctcc atcagtgtat     600
tacaactact acgaccccag cgcaactccg ccggcgggcg agctggacgg gtctaatgtt    660
ccgtctcagg cgatgcacga taatccaggt acgtccggcg gattgcccga ctggtttgcg    720
ctgccactcg accagttttt caacagttcg acagccgtgg tggaccaggg tctgggaggc    780
acgggcccca tggtgggcga atttgacatg ctggaggtgc ttctaaatga acagtatgac    840
ggtcatgagg ggatagagtc ggctggcgga gggaaccttc cgtcacagtt tttgcaatcg    900
tgatcaccga tggtctcatg aatgtacgaa tttacgcgtc gtagcttctt cctcttttg     960
cttggattct tgctagttcc tttctgtaca cttccgcttt tggcttgtga tcttgattgc   1020
tagagatgta tatcctcacg gataccgccg gagtgcgcca tttctggtta ccttctcttt   1080
cccttttgt ctcgatcgtg aggcggaacg caggatgaag acacggcttc tccatcgcgg   1140
cccaccaacc aacaatgtcc ttggacgccc aactctccat ctactggtca ttggtccaat   1200
gcagagacac cgtcgagctc aaatgggccg gccaaccccg agtcgtcagg ggcagcggca   1260
gcaacgagct aaattagacc actgataaga cgcgatagtc caaagtctga ccgtcacatt   1320
gtgccagcag ataagttgaa tcgtgtgact ggatgttggc taacgtatgg cgtctccgga   1380
ggcccgacgg accctgcgcg atcggcggtg agcgcaatc taaggacatc cgcgcctaag   1440
atatctaccc ttcagcagtt cagcctagcc ctgcagactt gtcggaccag tgctatcgtg   1500
atcggccccc acgtcgaat gagctcttgt ctctttccgt cagaccctgc cagttaatct   1560
gctatctact ccgcggtaac atcgtgcctg tctccactaa ggcagggtcc agggctgtat   1620
gtcttacttt gcaccgagtc ggccgccggt tggctctgtc ttggcaattg cgaatatcct   1680
cacgggcgac ggacgacacg gatttggacg gacatgcgga gatcttcgtc ggtttattcc   1740
tggaagggac atcatctcct tccatcatga cggctgccat agcggggact ctgagacatt   1800
tttgctctga agagcatggt cgacttggat gatggaggag ttgatcgagg tcaatgagga   1860
gaggcttgca agtataagaa gagactgctc gaccagcaga atggatcttc ttgttcatca   1920
accaagagtc caaggcttct ttgtctggtt ctatctcttc tccgaactct cttgcttgac   1980
attctagagg tcaaaatgcg aggattatac tccctcggcg ccttcgccag tctcattgcg   2040
gcggcttcgg ctgcatgccc aatgctgact ggcgaaatcc cagctggtag tgttgccaat   2100
cctcatcatc acggaaagcg tgacgattca aatgcttcct ccgaaacaga agcctttctg   2160
tccgagttct acctcaacga caacgatgcc tatctcacca ccgatgtagg cggtccgatc   2220
gaggatcaaa acagtttgaa ggccggcatt cgtggatcga ccctcttgga agacttcatc   2280
ttccgtcaga aaatccagca ttttgatcat gagcgtgtag gttatccatt ctatcacgta   2340
cttcaggggt agttctgaca tgcccaggtc ccggaacgtg ccgtgcatgc tcgaggtgca   2400
ggtgctcatg gtgtatttac ttcatatgcc gactggtcca acatcactgc tgcttcattt   2460
ttgggagctt ccggaaagga aacgcccaca tttgtccgct tctcgactgt tgcaggcagc   2520
cgaggaagtg ccgacaccgc tcgtgacgtt cacggatttg ctactcgctt ctatactgac   2580
gagggaaact atggtagcct ttctctttga ctcgtccata gatagggatg taactgactt   2640
caacagacat tgttggaaac aacattcctg tcttcttcat ccaagatgct atcttattcc   2700
cagatctcat cctatagcgtt aagccacagc cagccaatga aatcccacag gctgctactg   2760
cacacgacac ggcctatgac ttctttggtc aacagccaag cactctgcat accctcttct   2820
```

```
gggcaatggc aggccatggt atcccacggt cttccgtca tgttgacgga ttcggtgtcc   2880
acacctatcg gttcgtgaca gatgatggct cgtccaagtt ggtcaaattt cactggacat   2940
cgctgcaagg tcgggccagt ctggtctggg aggaagctca ggccactgct ggcaaaaatg   3000
ccgactttat gagacaggat ctgtatgata gcattgaggc tggccgttat ccagagtggg   3060
aggtatgtac caccgaattc atggaaagta ctcgactaac gtgaacagct cggcgtgcaa   3120
ataattgagg agtcggatgt cttaagctac ggatttgacc tgttggatcc aaccaagatt   3180
cttccggttg aaaaagttcc aattactgcg ctcggaaaaa tgcaactcaa ccgtaatcca   3240
ttgaattact ttgccgagac agagcaagtc atggtaagtc gaccttccgg cactcgagtc   3300
atttcctact aacgtggata gttccaacct ggccacattg ttcgtggtat cgacttcacc   3360
gaggatcctc ttctccaggg tcgtttattc tcctacctcg atactcagct gaatcgcaat   3420
ggtggtccca actttgaaca aattccaatc aatcgtccgc gtgttcctat ccacaacaac   3480
aaccgcgatg gattcgccca atgtttatt cctttgaacc aggcagcata ttcacccaac   3540
accttgaata atggctctcc tcgacaagcc aacgagactg tcggaaatgg cttctttacc   3600
gcccccgggc gctccgcaga tggacacctt gttcgcgcta cgagcccaac atttgccgac   3660
gtgtggtctc agcctggctt gttttacaac tccttgacgg ctaccgaaca acagttcgtg   3720
atcaatgctt tgcgtttcga attgtctaat gtaaagagcg aggatgttaa aagcaatttc   3780
atcacacaga taaatcgcgt aaacaacacg ttagcaacac ttgtggcttc tgcaattgga   3840
gtctccgcgc ccgaacccga ctctacatac taccacagca ataagacgtc taatgtcgga   3900
acattcggta ctccgttgaa aaagcttgac ggtctcaagg tcggagtcct tgcttcggtg   3960
aacggtgaaa gtagtattgc cgagggacaa gcattggcac aaagcctagc gggctcgaac   4020
gtggacgtcg ttatcgtcgc cgagcatctt acttcgaacg tgtcagctac atactctgga   4080
tcagacgcaa cgaactttga tgctgttatt gtcagctcag gggctgaagg tctctttgga   4140
cctcaaacct ttacagccga atccaataca acactttatc cggcaggccg tcctagccag   4200
attttggtcg atgccttccg ctttggcaag ccggttggag cagttggtgg tgccagtgca   4260
gctctgtcag cggtggatat cagtactgat cgtagtggtg tgattactgg tgattccgtc   4320
agtgacgact ttgtcaagca gctaacggag gaccttgcca cattcaaatt cttggaccga   4380
ttcgctgtgg atgagtagtc tagaatcaac cactgaagtg gagtctataa tctgctgatt   4440
gatccctcga cgatgaacta catgtggaaa tgtatagcag acgagggtga tggtgatgat   4500
gttgatttga tgatgacccg tacatacttg atgaagctcg gtacatatgc aaatgtgact   4560
gtatctatgt gatgaatata tatatatata tgtatatcca tctcatggct tttggctatg   4620
agtgcaggat aaaacctga accagtagta gtactttccc acctatatct actgcggtgc   4680
ctcgtccggc ccaacatcac cccagaggtg gccgcagagg agtcttataa gatagctact   4740
atcagttaca acacctctct gacagatgtg aaggagtaca ataaatcacc gaaacacaaa   4800
ttcaactaaa atcggtaagt aataataatt taagacccaa tccacgcaat gttaaactat   4860
ctctggtgtt gaaagatctc tccctggca acacctagtt gtgggagaac tgtgtttgcc   4920
tgcctatagt tccgttgacg ctccgtggga agtgcagtt acataaatat attaagaaag   4980
tagagttgta gtttagatta ttaataagtt tcaatagtct agtcctctac aatcgcacag   5040
ttaaaatatt atcatgtcaa taagcaaaac tgccatagag atagtagtaa gttcctggcg   5100
aagaagttgt gaacttgcct ggaattgaga aaattgggga cgggcgcgtt agatagggac   5160
```

```
cgacgcccaa atgaaccaca tcaaataagt caattttttgg aaaccgtttc tacacaagta    5220
gcccttgtgg cgcaatcggt agcgcgtaag acttctaatc ttaaggctgt gggttcgacc    5280
cccaccaggg gcttttttttt atttatctttt ttccccttttg atttcgcatt caacttcaag    5340
cttttttgaa acatatgagg cgcctcccctt atgtccttttt cctttccttc tttctttctt    5400
atgtcatctc gtccttctgc tatcaatcaa agaaatatct gccctctcca aacgtgactt    5460
gtttgcgcaa ttaacatcat gcttcatatt cacatgaacg gcccgctcac ttgctttttt    5520
tgtctaacct caagcaagaa gctgctgtga atgcaagcta atatggcatg atattgtacc    5580
cgccattaac caaggaggcc cttgtggcgc aatcggtagc gcgtaagact tctaatctta    5640
aggctgtggg ttcgaccccc accaggggct ttacatttttt ttcatttttct ttttggtaca    5700 ttccttcctt attttttcgta gtattacctt aagaaactat aattgactaa ctgggctggg    5760
tcatgataat gttattgaca gtatactgcc tagcaagatg gtgtttttata atatcaatca    5820 gctcctcccc cccttcctcc ggcgaattc gagatagacg ctgaatgttc actgcaacaa    5880
aggaaaggga aggaagaggg ggggcgggta catggaaaat cacatcaaca cacgattaac    5940
gaggcagtgg actggtatgt gccccacgcc taaatcgttc aagcaaagga tgagcagtat    6000
tttcattacc aatgtggata aaccgtctcg ggaactgcga gatctcttcc aatgatttct    6060
tctccagaac ctccacgaag gtgttcgcct tgaataccat acccatggcc gaatttgttg    6120
catagtatac cacttcacga ccgaaggaat cggtgtatct aatccggaaa gctagacgga    6180
gggccggatc atcatgagct tcagagcttg aggttgcata tagacttgta tgcgtttctc    6240
cccaaggaca aagctccagt ttgacaaaga ccttttccatc catgatatcc atatcatccg    6300
ggaatagaat ctcgcaatag taaatattag aagctaagtt gagacgatac agccccaagc    6360
ttcaggtaag tgagtagcca gtataagatt aaatcgagct aatagcctgg gagcatacgg    6420
taagcccaaa gagatcatat actgatcatt agtgatgtga ctccatttgg caattcctct    6480
cgtttaaaac gctgatagga taaaaccatt aatactagta tcgcagtatc acgaagtatc    6540
gggtatgaat cctcaaacaa ctccagcgga gagagtagta tcgtcccatg ccttaggcga    6600
attcactggc cgtcgtttta caacgtcgtg actgggaaaa ccctggcgtt acccaactta    6660
atcgccttgc agcacatccc cctttcgcca gctggcgtaa tagcgaagag gcccgcaccg    6720
atcgcccttc ccaacagttg cgcagcctga atggcgaatg gcgcctgatg cggtattttc    6780
tccttacgca tctgtgcggt atttcacacc gcatacgtca aagcaaccat agtacgcgcc    6840
ctgtagcggc gcattaagcg cggcgggtgt ggtggttacg cgcagcgtga ccgctacact    6900
tgccagcgcc ttagcgcccg ctcctttcgc tttcttccct tcctttctcg ccacgttcgc    6960
cggctttccc cgtcaagctc taaatcgggg gctccctttta gggttccgat ttagtgcttt    7020
acggcacctc gaccccaaaa aacttgattt gggtgatggt tcacgtagtg gccatcgcc    7080 ctgatagacg gttttttcgcc ctttgacgtt ggagtccacg ttctttaata gtggactctt    7140
gttccaaact ggaacaacac tcaactctat ctcgggctat tcttttgatt tataagggat    7200
tttgccgatt tcggtctatt ggttaaaaaa tgagctgatt taacaaaaat ttaacgcgaa    7260
ttttaacaaa atattaacgt ttacaatttt atggtgcact tcagtacaa tctgctctga    7320 tgccgcatag ttaagccagc cccgacaccc gccaacaccc gctgacgcgc cctgacgggc    7380
ttgtctgctc ccggcatccg cttacagaca agctgtgacc gtctccggga gctgcatgtg    7440
tcagaggttt tcaccgtcat caccgaaacg cgcgagacga agggcctcg tgatacgcct    7500 attttttatag gttaatgtca tgataataat ggtttcttag acgtcaggtg gcacttttcg    7560
```

```
gggaaatgtg cgcggaaccc ctatttgttt attttttctaa atacattcaa atatgtatcc    7620
gctcatgaga caataacccct gataaatgct tcaataatat tgaaaaagga agagtatgag    7680
tattcaacat ttccgtgtcg cccttattcc ctttttttgcg gcattttgcc ttcctgtttt    7740
tgctcaccca gaaacgctgg tgaaagtaaa agatgctgaa gatcagttgg gtgcacgagt    7800
gggttacatc gaactggatc tcaacagcgg taagatcctt gagagttttc gccccgaaga    7860
acgttttcca atgatgagca cttttaaagt tctgctatgt ggcgcggtat tatcccgtat    7920
tgacgccggg caagagcaac tcggtcgccg catacactat tctcagaatg acttggttga    7980
gtactcacca gtcacagaaa agcatcttac ggatggcatg acagtaagag aattatgcag    8040
tgctgccata accatgagtg ataacactgc ggccaactta cttctgacaa cgatcggagg    8100
accgaaggag ctaaccgctt ttttgcacaa catgggggat catgtaactc gccttgatcg    8160
ttgggaaccg gagctgaatg aagccatacc aaacgacgag cgtgacacca cgatgcctgt    8220
agcaatggca acaacgttgc gcaaactatt aactggcgaa ctacttactc tagcttcccg    8280
gcaacaatta atagactgga tggaggcgga taaagttgca ggaccacttc tgcgctcggc    8340
ccttccggct ggctggttta ttgctgataa atctggagcc ggtgagcgtg gtctcgcgg    8400
tatcattgca gcactggggc cagatggtaa gccctcccgt atcgtagtta tctacacgac    8460
ggggagtcag gcaactatgg atgaacgaaa tagacagatc gctgagatag gtgcctcact    8520
gattaagcat tggtaactgt cagaccaagt ttactcatat atactttaga ttgatttaaa    8580
acttcatttt taatttaaaa ggatctaggt gaagatcctt tttgataatc tcatgaccaa    8640
aatcccttaa cgtgagtttt cgttccactg agcgtcagac cccgtagaaa agatcaaagg    8700
atcttcttga gatccttttt ttctgcgcgt aatctgctgc ttgcaaacaa aaaaaccacc    8760
gctaccagcg gtggtttgtt tgccggatca agagctacca actctttttc cgaaggtaac    8820
tggcttcagc agagcgcaga taccaaatac tgttcttcta gtgtagccgt agttaggcca    8880
ccacttcaag aactctgtag caccgcctac atacctcgct ctgctaatcc tgttaccagt    8940
ggctgctgcc agtggcgata agtcgtgtct taccgggttg gactcaagac gatagttacc    9000
ggataaggcg cagcggtcgg gctgaacggg gggttcgtgc acacagccca gcttggagcg    9060
aacgacctac accgaactga gatacctaca gcgtgagcta tgagaaagcg ccacgcttcc    9120
cgaagggaga aaggcggaca ggtatccggt aagcggcagg gtcggaacag gagagcgcac    9180
gagggagctt ccagggggaa acgcctggta tctttatagt cctgtcgggt ttcgccacct    9240
ctgacttgag cgtcgatttt tgtgatgctc gtcagggggg cggagcctat ggaaaaacgc    9300
cagcaacgcg gcctttttac ggttcctggc cttttgctgg ccttttgctc acatgttctt    9360
tcctgcgtta tccctgatt ctgtggataa ccgtattacc gcctttgagt gagctgatac    9420
cgctcgccgc agccgaacga ccgagcgcag cgagtcagtg agcgaggaag cggaagagcg    9480
cccaatacgc aaaccgcctc tccccgcgcg ttggccgatt cattaatgca gctggcacga    9540
caggtttccc gactggaaag cgggcagtga gcgcaacgca attaatgtga gttagctcac    9600
tcattaggca ccccaggctt tacactttat gcttccggct cgtatgttgt gtggaattgt    9660
gagcggataa caatttcaca caggaaacag ctatgaccat gattacgcca agcttgcatg    9720
cctgcagg                                                             9728
```

<210> SEQ ID NO 22
<211> LENGTH: 21
<212> TYPE: DNA

```
<213> ORGANISM: Artificial Sequence
<220> FEATURE:
<223> OTHER INFORMATION: primer : Nia-N

<400> SEQUENCE: 22
atggcgactg tcactgaggt g                                              21

<210> SEQ ID NO 23
<211> LENGTH: 21
<212> TYPE: DNA
<213> ORGANISM: Artificial Sequence
<220> FEATURE:
<223> OTHER INFORMATION: primer : Nia-C

<400> SEQUENCE: 23
ttagaagaaa tgaaggtccg a                                              21

<210> SEQ ID NO 24
<211> LENGTH: 6416
<212> TYPE: DNA
<213> ORGANISM: Artificial Sequence
<220> FEATURE:
<223> OTHER INFORMATION: Aspergillus niger var. macrosporus

<400> SEQUENCE: 24
tctagacgtc cactcactga ctactgactc ctgactgact agtagtcggc cgatgggacc      60
atttcttttc ttccatcttt tcctgctcgc ccccactgcg gcaaaaagct caacagtccc     120
aggcaatatt acttgctcaa taatccccga taccgtgaat acacgattaa tcacggtcaa     180
ctggagactt cgtaatcctg ctgcatttaa tgggcaatta atcggcggtg gagccctttg     240
gaaactaaag tggatctggc cgctgtcctc ctggggcttg ttttgccatt acagcacaaa     300
ttgtcactag tatcgagttt agtttagtga gtctgcttgc tgctcgggag aggcttgttt     360
ccagtttttt ttttcatgcc tggttttttta actttttttt tttcgggacc aggtctcaag     420
ttcccacatt cccggtagga atgttcgaat gagaagcccg tgttctccct gtctacccga     480
caggaggaca caccaggcca tgactagacc tgctggagag tacggagtat tactattaca     540
tatctctgct tgttagttaa ctcattgttc gaatccaccg gctcccgcgg aaatctctcc     600
ggccgaatgt tggccctcac tcacgccctc cccccaaaa tagatctcaa accaggtgga     660
atacctcctg tttcttctcc gtggacttag taccagatcc cggccgttgc tggtcacacc     720
ccgttgagct aatccaaaag ccggcagttt tgagggttca tctgtcatct ggtttttgag     780
cgattaattt tcccgtagct aaccctgatc ttccccggat gagtgtcttg ctcctctcat     840
ctgccttctg catgctctgt atcggtccta agctatactc gtcttcatcc ctgatattgt     900 ctcatgccttt atttggcacc tcgaggccat tgaaccacat aaacacatac catggcgact     960
gtcactgagg tgctgacaga gcctttcacc gctcaagggg tcaccctcaa gtcgggtccg    1020
atcaaggtcc accaggagga gttgcctgcc gtggaacttt cagacattcc tctgccgccc    1080
ccgtcaaaag agccaaccga ggtcctcagt atagacaagc caaccccga ttatcatgtt    1140 ccgcgcgacc ctcgccttat cagactgacc ggtgttcatc ccttcaatgt cgagcctcca    1200 ctcacgcgc tgtacgacga aggtactcaa cgtctttcct gccgccccgc tcttttttgaa    1260 ctcggcgcaa acttccttgt attcgtagcg atgctccacct gccaataggc ttcttgactt    1320
ccccggaact gttctatgtg agaaatcatg gcccggtacc attggtgaag gacgaagata    1380 tcccccaattg ggagattagc atcgaagggt aaggaatctc gatttcctca aacatcgcgt    1440
catcatctga caatggatat gcagcctggt ggagaagccg cttgtcctca acttccggga    1500
```

```
cattttgcag caatacgatc agatcacagc accaatcact ctcgtctgtg cgggaaacag   1560
acggaaggag cagaatgtgg tcaggaagac caaaggtttc tcatgggtt  ctgccggcct   1620 gtcgacggct ctctggactg gcccaatgat ggcagatatc ctacggagtg cgaagccttt   1680
gaggaaagcc aagtatgtct gcatggaggg agctgataag ctggtaagtt accttatcca   1740
tccatgcatg cagtgccctg acagtttgct ttcagccaaa cgggtattac gggacatcga   1800
tcaaactcaa ttgggccatg atcccaata  ggggaatcat gctggcccac aaaatgaatg   1860
gcgaggatct ccgtcctgat cacggccgtc ccttgagggc tgtcgtaccc ggccagatcg   1920
gtggccgaag tgtcaaatgg ctgaagaagc tcattctcac tgatgcgccc agtgataact   1980
ggtaccacat ctatgacaac cgagtattac cgtgagactt gcctatccga ccacaagagt   2040
acgttgtcta actgttatcc aggacaatgg tttcgcctga atgtcgtcc  agtgacccaa   2100 cttggtggcg cgacgaccga tatgcgattt atgatcttaa cgtgaactct tctgttgtat   2160
accccgagca taaggaggtg ctggatcttg cgtcggcagg cccgtcgtac aacgtgaaag   2220
gatatgccta tgcaggaggc ggtcggagga ttacgagagt cgaaatatct ttagacaaag   2280
gcaaatgtac gacgatcatt gcgcaaatgt gttgaggcag agctaacatg ttttagcct   2340 ggcgattggc caacatctca tatgccgaag acaagtatcg tgactttgaa ggggacttgt   2400
ttggtggtag agtggacatg tcctggcgcg agacttgttt ctgctggtgc ttctggtcgc   2460
tggatatcgc cattcctgag ctagaaaata cagatgccat tctcgtgcga gccatggatg   2520
aggccttggc tctccaacca cgcgatatgt attggtctgt tctgggcatg atgaacaatc   2580
cttggttccg ggtcaccatc acgaaggaga acgggactct caggttcgag cacccaacag   2640
atcctactgg gcccggcgga tggatggagc gcgtcaaaaa ggccgggggt gatctggtca   2700
atggttactg gggagaacga caagcaggag aggaaccgac agagcctgag cctgagaagg   2760
agatcaacat gaagaaagag ggcgtgaacc ggattatcga ccttcaagaa ttcaagaaga   2820
actcaagcga tgagaagccc tggttcatcg tgaacggtga agtgtacgac ggcacggcat   2880
tcctggaggg ccatccggga ggagctcaga gtatcatctc gtctgctggc atcgacgttt   2940
ctgaggaatt tttggcaatc cgtacgtcct agggaccttc gaacaatgga aattagaatg   3000
ctgacacacc cacagatagc gaaacagcca aagccatgat gcccgattac catatcggaa   3060
ccatggataa ggcgtccttg gaagcgctca agaacgacaa cgcaccacaa tcggatgaac   3120
ctcgtgcaac attccttcag tcgaaatcat ggacaaaggc aacacttgta agaggacgg   3180 acgtgtcctg ggacacgcgg attttcactt tccagctcca acacgacaaa caaccctgg   3240 gtctgcccat tggccagcat ctcatgatca aggtcgccga ccctaccagc aaagaagtca   3300
tcatccgctc atacccct   atctccgata ccaaccagga aggcaccatg gacctgctgg   3360
tcaagatcta cttcgacacg cccacagtca aggtggcaa  gatgaccatg gccttagaga   3420
agctcgcgtt gggatcagaa atcgactgca agggtcccac tggtaggttt gagtaccttg   3480
ggaacggcaa gatcttggtg agcgggaaag agcgccatgt tagttctttt aagatgattt   3540
gcggtggaac tggtatcacg ccaatcttcc aagtgctacg tgcggtgatg caggacaagc   3600
aggaccctac gtcatgcgtg gtcctggatg caaatagaca ggaagaggac atcctctgcc   3660
gcgccgatct ggacgcctat gaagcgttgg atagcaagaa gtgtaaggtg gtacacactt   3720
taaccaaggc tccggacagt tggactggac gccgtgacg  tatatcagaa gacctgctga   3780
aggagcacgc cattcccgat ggcaagagca tggtgcttat ctgtggtcca gaggccatgg   3840
```

-continued

```
aaaagtccgc caggaagatc cttctggagc aaggatgggc ggagtcggac cttcatttct    3900
tctaagggaa gcgcctcctc agtactggaa atagccttcg tcactagtat aggaagacga    3960
cattgttaga tgtatataag aacgctaatt ccacaagaaa tatgtacgaa ctgtgatgtt    4020
tttcaaattt gaaggctaaa attgggctcg aagtgcgcct gcaatatgcg cgagtcagac    4080
gtaggatcgt ctaccagtgt cagaatcgtc tcattcgttt actcacgtca gtcatttaag    4140
acaagtagtc ggtcctgctt tataaggaaa gcgactgtca actaaatggc gtcgcactat    4200
agtcacttca tctccaaacg ggccacacgg agacagtcgc tggcgctttt ctggatgtaa    4260
atgctatacc cgacgtttca agaaccttg  acacgttct  ataccgcgta agcagcgaat    4320
agaggtagaa gttttgtttc actcatccga cgactgacag gttcaacgtc gtggcgcaca    4380
ccaagattcc attcagcgga gagcgagcgt agggaatcct tcgaagatat aacggaggtt    4440
tcgtacgttc atcgtacttt attctaaaac aattccctgc cgtatttctg aatcgcactc    4500
gaaaaggcac ttgaagcaat tcgcaatccg accctattaa tgacgtcttt cagcatatgg    4560
ttagtagtat ggagcagaca acttctccca cggcaacagc ttcaatggat gcaggaaccg    4620
ccagataaac ctgtcaatca tccacagatc atgaccatac agcgggccaa cagtggagtc    4680
tcccgtattc atcgttctta ctcgaacaca gcccaccaaa acctcgtggg aatctcaagt    4740
gacaaccacc agacgacgcg ttggcagcgc gagatcacgc ctcactaaac ccgaaccaga    4800
ctagtgcctc tccccgtcca acgcccggac caccgcttgt tcgggaaacc gaagcggcag    4860
gaattcgccg cggttcaacc aacccgcgga cgagagctct cccctccgtc ccctcagaaa    4920
taacattatt taccttatcc acctctacac acaaagtctc tctttacgca ccaatcaatc    4980
gccatgcccc cgcgcaagaa agccaaactt acccccccaaa gcgagaatgc cgagccgtcc    5040
gcaagcacca ctgaccagcc aacaaccgcg gattacgacc cagtgacaga tccctggacg    5100
gacgagcaag agaccgcgtt attgaagggg attataaaat ggaagcctgt cggtacgttg    5160
accgcaaccc ttctccccgc gcgcgcaggg gaaacactat catcggagca gtgtgacgct    5220
aacgcggccc tctttctctt tcaaaaggca tgcacaagca cttccgtatg atcgcgattt    5280
cggagttcat gaaaagccaa ggctatgcgc ccgcgcacgc agaacacaca cggataccgg    5340
ggatatggaa gaagctgggg acattataca atcttccggc tttggatgaa cgggtgggtt    5400
gatgccctct ctcatccatg gagattacgt cctttggatt ctggctcgtg ctaacattca    5460
tctaatatta cggaatgagc aggaagattc attgataaca gacaccgccg aggactcaaa    5520
ggaattctac tgcccgttcg aattacccca ggatgaatac ggagaattga tgttcgaacg    5580
gcggctggcg atggaaggaa ccgcatctcc tgatcctagc acgcatgcgg gatcgaggag    5640
ggggagcacg gtggctgata cggacggtgc gtatataata tctctgcctt ggttgtcaac    5700
tggttgttgg ggaaagcgta ctaatcgcaa tcgattcatc tcatacagaa cctcgctctt    5760
cccccgcgcc atcacgagga cggaagtcag gtcgtggcgg gcgtccagcg ggacgaggga    5820
cgcgttcgtc gcgtcttcat gtggaggtcg aaccgccggc gaagggatcc ggagctgcgg    5880
aggaagaagc ggattctggc gaggagacag gcgcaaatga agaaggcgat gaagatggtt    5940
cggacgctgc gaaggatgat agtgaggtcg atgaggaagc ggagggggc  tcgcctacga    6000
cgcgaagtac gcgtgcccag acatcgagga cgaagcagaa gggcagaggt acagcaggca    6060
cgggaactcg gaggggtcga cggcgtcagc cttgatattg atatgtgctt tctgctgacg    6120
ttcgttggct ctgtctgtaa caaatacgtc gctaatgata ccttgggaga aataggcgtt    6180
ttggtggggc tttgtttgta tgattacttt tctccttctt tgttctacca tccattgttc    6240
```

```
ttttgccgga cggtacgcta tgcatactcc gttgatcaag ccattggctt gtatctttct    6300
atctccaacg acgacagttg gagaatagga aatccgagat aggaagtaaa acaacataga    6360
tggcatctaa atacatggga gcacatacaa tagatcacta catatttggg tctaga        6416
```